(12) United States Patent
Etzkorn et al.

(10) Patent No.: US 10,004,457 B2
(45) Date of Patent: *Jun. 26, 2018

(54) ENCAPSULATED ELECTRONICS

(71) Applicant: Verily Life Sciences LLC, Mountain View, CA (US)

(72) Inventors: James Etzkorn, Mountain View, CA (US); Babak Amirparviz, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/278,853

(22) Filed: Sep. 28, 2016

(65) Prior Publication Data
US 2017/0014074 A1    Jan. 19, 2017

Related U.S. Application Data

(63) Continuation of application No. 14/518,986, filed on Oct. 20, 2014, which is a continuation of application
(Continued)

(51) Int. Cl.
*A61B 5/05* (2006.01)
*A61B 5/00* (2006.01)
(Continued)

(52) U.S. Cl.
CPC .......... *A61B 5/6821* (2013.01); *A61B 5/0002* (2013.01); *A61B 5/0004* (2013.01);
(Continued)

(58) Field of Classification Search
CPC ......... A61B 5/00; A61B 5/145; A61B 5/1468; A61B 5/14532; A61B 5/0002;
(Continued)

(56) References Cited

U.S. PATENT DOCUMENTS

| 3,958,560 A | 5/1976 | March |
| 4,014,321 A | 3/1977 | March |

(Continued)

FOREIGN PATENT DOCUMENTS

| CN | 1589122 | 3/2005 |
| EP | 0369942 | 5/1990 |

(Continued)

OTHER PUBLICATIONS

Badugu et al., "A Glucose Sensing Contact Lens: A Non-Invasive Technique for Continuous Physiological Glucose Monitoring," Journal of Fluorescence, Sep. 2003, pp. 371-374, vol. 13, No. 5.

(Continued)

*Primary Examiner* — Navin Natnithithadha
*Assistant Examiner* — Eric Messersmith
(74) *Attorney, Agent, or Firm* — McDonnell Boehnen Hulbert & Berghoff LLP

(57) ABSTRACT

An eye-mountable device includes an electrochemical sensor embedded in a polymeric material configured for mounting to a surface of an eye. The electrochemical sensor includes a working electrode and a reference electrode that reacts with an analyte to generate a sensor measurement related to a concentration of the analyte in a fluid to which the eye-mountable device is exposed. An example assembly process includes: forming a sacrificial layer on a working substrate; forming a first layer of a bio-compatible material on the sacrificial layer; providing an electronics module on the first layer of the bio-compatible material, forming a second layer of the bio-compatible material to cover the electronics module; and annealing the first and second layers of the bio-compatible material together to form an encapsulated structure having the electronics module fully encapsulated by the bio-compatible material.

20 Claims, 12 Drawing Sheets

Related U.S. Application Data

No. 13/741,725, filed on Jan. 15, 2013, now Pat. No. 8,874,182.

(51) Int. Cl.

| | | |
|---|---|---|
| *A61B 5/145* | (2006.01) | |
| *A61B 5/1486* | (2006.01) | |
| *A61B 5/1473* | (2006.01) | |
| *A61B 5/1468* | (2006.01) | |
| *A61B 5/1455* | (2006.01) | |
| *H01L 23/31* | (2006.01) | |
| *H01L 21/56* | (2006.01) | |
| *G01N 27/327* | (2006.01) | |
| *G02C 7/04* | (2006.01) | |

(52) U.S. Cl.
CPC .......... *A61B 5/1455* (2013.01); *A61B 5/1468* (2013.01); *A61B 5/1473* (2013.01); *A61B 5/1486* (2013.01); *A61B 5/14507* (2013.01); *A61B 5/14532* (2013.01); *A61B 5/6867* (2013.01); *H01L 21/568* (2013.01); *H01L 23/3107* (2013.01); *A61B 5/14865* (2013.01); *G01N 27/3271* (2013.01); *G02C 7/04* (2013.01); *H01L 2224/81001* (2013.01); *Y10T 29/49826* (2015.01)

(58) Field of Classification Search
CPC ... A61B 5/1486; A61B 5/6821; A61B 5/1473; A61B 5/6867; A61B 5/14507; A61B 5/1455; A61B 5/0004; H01L 23/3107; H01L 21/568; G01N 27/3271
See application file for complete search history.

(56) References Cited

U.S. PATENT DOCUMENTS

| | | |
|---|---|---|
| 4,055,378 A | 10/1977 | Feneberg et al. |
| 4,122,942 A | 10/1978 | Wolfson |
| 4,136,250 A | 1/1979 | Mueller et al. |
| 4,143,949 A | 3/1979 | Chen |
| 4,153,641 A | 5/1979 | Deichert et al. |
| 4,214,014 A | 7/1980 | Hofer et al. |
| 4,309,085 A | 1/1982 | Morrison |
| 4,312,575 A | 1/1982 | Peyman et al. |
| 4,401,371 A | 8/1983 | Neefe |
| 4,463,149 A | 7/1984 | Ellis |
| 4,555,372 A | 11/1985 | Kunzler et al. |
| 4,604,479 A | 8/1986 | Ellis |
| 4,632,844 A | 12/1986 | Yanagihara et al. |
| 4,686,267 A | 8/1987 | Ellis et al. |
| 4,740,533 A | 4/1988 | Su et al. |
| 4,826,936 A | 5/1989 | Ellis |
| 4,921,205 A | 5/1990 | Drew, Jr. et al. |
| 4,996,275 A | 2/1991 | Ellis et al. |
| 4,997,770 A | 3/1991 | Giles et al. |
| 5,032,658 A | 7/1991 | Baron et al. |
| 5,034,461 A | 7/1991 | Lai et al. |
| 5,070,215 A | 12/1991 | Bambury et al. |
| 5,135,297 A | 8/1992 | Valint et al. |
| 5,177,165 A | 1/1993 | Valint et al. |
| 5,177,168 A | 1/1993 | Baron et al. |
| 5,219,965 A | 6/1993 | Valint et al. |
| 5,260,000 A | 11/1993 | Nandu et al. |
| 5,271,875 A | 12/1993 | Appleton et al. |
| 5,310,779 A | 5/1994 | Lai |
| 5,321,108 A | 6/1994 | Kunzler et al. |
| 5,326,584 A | 7/1994 | Kamel et al. |
| 5,336,797 A | 8/1994 | McGee et al. |
| 5,346,976 A | 9/1994 | Ellis et al. |
| 5,358,995 A | 10/1994 | Lai et al. |
| 5,364,918 A | 11/1994 | Valint et al. |
| 5,387,662 A | 2/1995 | Kunzler et al. |
| 5,449,729 A | 9/1995 | Lai |
| 5,472,436 A | 12/1995 | Fremstad |
| 5,512,205 A | 4/1996 | Lai |
| 5,585,871 A | 12/1996 | Linden |
| 5,610,252 A | 3/1997 | Bambury et al. |
| 5,616,757 A | 4/1997 | Bambury et al. |
| 5,682,210 A | 10/1997 | Weirich |
| 5,708,094 A | 1/1998 | Lai et al. |
| 5,710,302 A | 1/1998 | Kunzler et al. |
| 5,714,557 A | 2/1998 | Kunzler et al. |
| 5,726,733 A | 3/1998 | Lai et al. |
| 5,760,100 A | 6/1998 | Nicholson et al. |
| 5,908,906 A | 6/1999 | Kunzler et al. |
| 5,981,669 A | 11/1999 | Valint et al. |
| 6,087,941 A | 7/2000 | Ferraz et al. |
| 6,131,580 A | 10/2000 | Ratner et al. |
| 6,193,369 B1 | 2/2001 | Valint et al. |
| 6,200,626 B1 | 3/2001 | Grobe et al. |
| 6,213,604 B1 | 4/2001 | Valint et al. |
| 6,312,393 B1 | 11/2001 | Abreu |
| 6,348,507 B1 | 2/2002 | Heiler et al. |
| 6,366,794 B1 | 4/2002 | Moussy et al. |
| 6,423,001 B1 | 7/2002 | Abreu |
| 6,428,839 B1 | 8/2002 | Kunzler et al. |
| 6,431,705 B1 | 8/2002 | Linden |
| 6,440,571 B1 | 8/2002 | Valint et al. |
| 6,450,642 B1 | 9/2002 | Jethmalani et al. |
| 6,532,298 B1 | 3/2003 | Cambier et al. |
| 6,550,915 B1 | 4/2003 | Grobe, III |
| 6,570,386 B2 | 5/2003 | Goldstein |
| 6,579,235 B1 | 6/2003 | Abita et al. |
| 6,599,559 B1 | 7/2003 | McGee et al. |
| 6,614,408 B1 | 9/2003 | Mann |
| 6,630,243 B2 | 10/2003 | Valint et al. |
| 6,638,563 B2 | 10/2003 | McGee et al. |
| 6,726,322 B2 | 4/2004 | Andino et al. |
| 6,735,328 B1 | 5/2004 | Helbing et al. |
| 6,779,888 B2 | 8/2004 | Marmo |
| 6,804,560 B2 | 10/2004 | Nisch et al. |
| 6,851,805 B2 | 2/2005 | Blum et al. |
| 6,885,818 B2 | 4/2005 | Goldstein |
| 6,939,299 B1 | 9/2005 | Petersen et al. |
| 6,980,842 B2 | 12/2005 | March et al. |
| 7,018,040 B2 | 3/2006 | Blum et al. |
| 7,131,945 B2 | 11/2006 | Fink et al. |
| 7,169,106 B2 | 1/2007 | Fleischman et al. |
| 7,398,119 B2 | 7/2008 | Lambert et al. |
| 7,423,801 B2 | 9/2008 | Kaufman et al. |
| 7,425,749 B2 | 9/2008 | Hartzell et al. |
| 7,429,465 B2 | 9/2008 | Muller et al. |
| 7,441,892 B2 | 10/2008 | Hsu |
| 7,443,016 B2 | 10/2008 | Tsai et al. |
| 7,450,981 B2 | 11/2008 | Jeon |
| 7,639,845 B2 | 12/2009 | Utsunomiya |
| 7,654,671 B2 | 2/2010 | Glynn |
| 7,699,465 B2 | 4/2010 | Dootjes et al. |
| 7,728,949 B2 | 6/2010 | Clarke et al. |
| 7,751,896 B2 | 7/2010 | Graf et al. |
| 7,785,912 B2 | 8/2010 | Zhan et al. |
| 7,799,243 B2 | 9/2010 | Mather et al. |
| 7,809,417 B2 | 10/2010 | Abreu |
| 7,878,650 B2 | 2/2011 | Fritsch et al. |
| 7,885,698 B2 | 2/2011 | Feldman |
| 7,907,931 B2 | 3/2011 | Hartigan et al. |
| 7,926,940 B2 | 4/2011 | Blum et al. |
| 7,931,832 B2 | 4/2011 | Pugh et al. |
| 7,964,390 B2 | 6/2011 | Rozakis et al. |
| 8,080,187 B2 | 12/2011 | Tepedino, Jr. et al. |
| 8,096,654 B2 | 1/2012 | Amirparviz et al. |
| 8,118,752 B2 | 2/2012 | Hetling et al. |
| 8,142,016 B2 | 3/2012 | Legerton et al. |
| 8,224,415 B2 | 7/2012 | Budiman |
| 8,608,310 B2 | 12/2013 | Otis et al. |
| 8,874,182 B2 | 10/2014 | Etzkorn et al. |
| 8,886,275 B2 | 11/2014 | Etzkorn et al. |
| 2002/0193674 A1 | 12/2002 | Fleischman et al. |
| 2003/0179094 A1 | 9/2003 | Abreu |
| 2004/0027536 A1 | 2/2004 | Blum et al. |
| 2004/0116794 A1 | 6/2004 | Fink et al. |
| 2005/0045589 A1 | 3/2005 | Rastogi et al. |

(56) References Cited

U.S. PATENT DOCUMENTS

| | | | |
|---|---|---|---|
| 2005/0221276 A1 | 10/2005 | Rozakis et al. |
| 2006/0235475 A1 | 10/2006 | Mech et al. |
| 2007/0016074 A1 | 1/2007 | Abreu |
| 2007/0030443 A1 | 2/2007 | Chapoy et al. |
| 2007/0121065 A1 | 5/2007 | Cox et al. |
| 2007/0188710 A1 | 8/2007 | Hetling et al. |
| 2008/0006939 A1 | 1/2008 | Logan et al. |
| 2008/0208335 A1 | 8/2008 | Blum et al. |
| 2008/0218696 A1 | 9/2008 | Mir |
| 2009/0033863 A1 | 2/2009 | Blum et al. |
| 2009/0036761 A1 | 2/2009 | Abreu |
| 2009/0057164 A1 | 3/2009 | Minick et al. |
| 2009/0076367 A1 | 3/2009 | Sit et al. |
| 2009/0102068 A1 | 4/2009 | Pellinen et al. |
| 2009/0118604 A1 | 5/2009 | Phan et al. |
| 2009/0189830 A1 | 7/2009 | Deering et al. |
| 2009/0196460 A1 | 8/2009 | Jakobs et al. |
| 2009/0204207 A1 | 8/2009 | Blum et al. |
| 2010/0001926 A1 | 1/2010 | Amirparviz et al. |
| 2010/0013114 A1 | 1/2010 | Bowers et al. |
| 2010/0016704 A1 | 1/2010 | Naber et al. |
| 2010/0028559 A1 | 2/2010 | Yan et al. |
| 2010/0072643 A1 | 3/2010 | Pugh et al. |
| 2010/0103368 A1 | 4/2010 | Amirparviz et al. |
| 2010/0109175 A1 | 5/2010 | Pugh et al. |
| 2010/0110372 A1 | 5/2010 | Pugh et al. |
| 2010/0113901 A1 | 5/2010 | Zhang et al. |
| 2010/0133510 A1 | 6/2010 | Kim et al. |
| 2010/0249548 A1 | 9/2010 | Muller |
| 2011/0015512 A1 | 1/2011 | Pan et al. |
| 2011/0028807 A1 | 2/2011 | Abreu |
| 2011/0040161 A1 | 2/2011 | Abreu |
| 2011/0055317 A1 | 3/2011 | Vonog et al. |
| 2011/0063568 A1 | 3/2011 | Meng et al. |
| 2011/0084834 A1 | 4/2011 | Sabeta |
| 2011/0116035 A1 | 5/2011 | Fritsch et al. |
| 2011/0157541 A1 | 6/2011 | Peyman |
| 2011/0157544 A1 | 6/2011 | Pugh et al. |
| 2011/0184271 A1 | 7/2011 | Veciana et al. |
| 2011/0274680 A1 | 11/2011 | Mazed et al. |
| 2011/0286064 A1 | 11/2011 | Burles et al. |
| 2011/0298794 A1 | 12/2011 | Freedman |
| 2012/0026458 A1 | 2/2012 | Qiu et al. |
| 2012/0038881 A1 | 2/2012 | Amirparviz et al. |
| 2012/0041287 A1 | 2/2012 | Goodall et al. |
| 2012/0041552 A1 | 2/2012 | Chuck et al. |
| 2012/0069254 A1 | 3/2012 | Burton |
| 2012/0075168 A1 | 3/2012 | Osterhout et al. |
| 2012/0075574 A1 | 3/2012 | Pugh et al. |
| 2012/0078071 A1 | 3/2012 | Bohm et al. |
| 2012/0088258 A1 | 4/2012 | Bishop et al. |
| 2012/0092612 A1 | 4/2012 | Binder et al. |
| 2012/0109296 A1 | 5/2012 | Fan |
| 2012/0177576 A1 | 7/2012 | Hu |
| 2012/0197101 A1 | 8/2012 | Telandro |
| 2012/0199995 A1 | 8/2012 | Pugh et al. |
| 2012/0201755 A1 | 8/2012 | Rozakis et al. |
| 2012/0245444 A1 | 9/2012 | Otis et al. |
| 2012/0259188 A1 | 10/2012 | Besling |
| 2012/0302861 A1 | 11/2012 | Marshall et al. |
| 2013/0041235 A1 | 2/2013 | Rogers et al. |

FOREIGN PATENT DOCUMENTS

| | | |
|---|---|---|
| EP | 0686372 | 12/1995 |
| EP | 1061874 | 12/2000 |
| EP | 1818008 | 8/2007 |
| EP | 1947501 | 7/2008 |
| EP | 1617757 | 8/2009 |
| EP | 2457122 | 5/2012 |
| JP | H11-147428 | 6/1999 |
| JP | 2007512859 | 5/2007 |
| JP | 2008161667 | 7/2008 |
| JP | 2009254892 | 11/2009 |
| JP | 2010516312 | 5/2010 |
| JP | 2011521759 | 7/2011 |
| KR | 10-0675706 | 2/2007 |
| RU | 2010138591 | 3/2012 |
| WO | 1995/004609 | 2/1995 |
| WO | 2001/13783 | 3/2001 |
| WO | 2001/016641 | 3/2001 |
| WO | 2001/034312 | 5/2001 |
| WO | 2003/065876 | 8/2003 |
| WO | 2004/060431 | 7/2004 |
| WO | 2004/064629 | 8/2004 |
| WO | 2006/015315 | 2/2006 |
| WO | 2009/094643 | 7/2009 |
| WO | 2009/105261 | 8/2009 |
| WO | 2010/096828 | 8/2009 |
| WO | 2010/105728 | 9/2010 |
| WO | 2010/133317 | 11/2010 |
| WO | 2011/011344 | 1/2011 |
| WO | 2011/034592 | 3/2011 |
| WO | 2011/035228 | 3/2011 |
| WO | 2011/035262 | 3/2011 |
| WO | 2011/083105 | 7/2011 |
| WO | 2011/163080 | 12/2011 |
| WO | 2012/035429 | 3/2012 |
| WO | 2012/037455 | 3/2012 |
| WO | 2012/051167 | 4/2012 |
| WO | 2012/051223 | 4/2012 |
| WO | 2012052765 | 4/2012 |

OTHER PUBLICATIONS

Carlson et al., "A 20 mV Input Boost Converter With Efficient Digital Control for Thermoelectric Energy Harvesting," IEEE Journal of Solid-State Circuits, Apr. 2010, pp. 741-750, vol. 45, No. 4.

Chu et al., "Biomedical soft contact-lens sensor for in situ ocular biomonitoring of tear contents," Biomed Microdevices, 2011, pp. 603-611, vol. 13.

Chu et al., "Soft contact lens biosensor for in situ monitoring of tear glucose as non-invasive blood sugar assessment," Talanta, 2011, pp. 960-965, vol. 83.

Ho et al., "Contact Lens With Integrated Inorganic Semiconductor Devices," MEMS 2008. IEEE 21st International Conference on. IEEE, 2008., pp. 403-406.

Lähdesmäki et al., "Possibilities for Continuous Glucose Monitoring by a Functional Contact Lens," IEEE Instrumentation & Measurement Magazine, Jun. 2010, pp. 14-17.

Lingley et al., "A contact lens with integrated micro solar cells," Microsyst Technol, 2012, pp. 453-458, vol. 18.

Parviz, Babak A., "For Your Eyes Only," IEEE Spectrum, Sep. 2009, pp. 36-41.

Saeedi, E. et al., "Self-assembled crystalline semiconductor optoelectronics on glass and plastic," J. Micromech. Microeng., 2008, pp. 1-7, vol. 18.

Saeedi et al., "Self-Assembled Inorganic Micro-Display on Plastic," Micro Electro Mechanical Systems, 2007. MEMS. IEEE 20th International Conference on. IEEE, 2007., pp. 755-758.

Sensimed Triggerfish, Sensimed Brochure, 2010, 10 pages.

Shih, Yi-Chun et al., "An Inductorless DC-DC Converter for Energy Harvesting With a 1.2-µW Bandgap-Referenced Output Controller," IEEE Transactions on Circuits and Systems-II: Express Briefs, Dec. 2011, pp. 832-836, vol. 58, No. 12.

Shum et al., "Functional modular contact lens," Proc. of SPIE, 2009, pp. 73970K-1 to 73970K-8, vol. 7397.

Stauth et al., "Self-assembled single-crystal silicon circuits on plastic," PNAS, Sep. 19, 2006, pp. 13922-13927, vol. 103, No. 38.

Yao, H. et al., "A contact lens with integrated telecommunication circuit and sensors for wireless and continuous tear glucose monitoring," J. Micromech. Microeng., 2012, pp. 1-10, vol. 22.

Yao, H. et al., "A Dual Microscal Glucose Sensor on a Contact Lens, Tested in Conditions Mimicking the Eye," Micro Electro Mechanical Systems (MEMS), 2011 IEEE 24th International Conference on. IEEE, 2011, pp. 25-28.

Yao et al., "A contact lens with embedded sensor for monitoring tear glucose level," Biosensors and Bioelectronics, 2011, pp. 3290-3296, vol. 26.

(56) References Cited

OTHER PUBLICATIONS

Yao, H. et al., "A Soft Hydrogel Contact Lens with an Encapsulated Sensor for Tear Glucose Monitoring," Micro Electro Mechanical Systems (MEMS), 2012 IEEE 25th International Conference on. IEEE, 2012, pp. 769-772.

Yeager et al., "A 9 µA, Addressable Gen2 Sensor Tag for Biosignal Acquistion," IEEE Journal of Solid-State Circuits, Oct. 2010, pp. 2198-2209, vol. 45, No. 10.

Zhang et al., "Design for Ultra-Low Power Biopotential Amplifiers for Biosignal Acquistion Applications," IEEE Transactions on Biomedical Circuits and Systems, 2012, pp. 344-355, vol. 6, No. 4.

Cheng et al., "Dry release of polymer structures with anti-sticking layer," Journal of Vacuum Science & Technology A, May/Jun. 2004, pp. 837-841, vol. 22, No. 3.

International Search Report and Written Opinion for International Application No. PCT/US2013/076019 dated Apr. 24, 2014, 13 pages.

Mohan et al., "Design of fully integrated wireless CMOS MEMS device for intraocular pressure measurement," A Thesis submitted to the Graduate Faculty of North Carolina State University in partial fulfillment of the requirements for the degree of Master of Science, May 10, 2008, 89 pages.

De Smet et al., "Design and Wrinkling Behavior of a Contact Lens With an Integrated Liquid Crystal Light Modulator," Journal of Display Technology, May 2012, pp. 299-305.

Bionic contact lens 'to project emails before eyes,' http://www.kurzweilai.netforums/topic/bionic-contact-lens-to-project-mails-before-eyes, Last accessed Mar. 14, 2012, 2 pages.

Brahim, et al., "Polypyrrole-hydrogel composites for the construction of clinically important biosensors," 2002, Biosensors & Bioelectronics, pp. 53-59, vol. 17.

Chen, et al., "Microfabricated Implantable Parylene-Based Wireless Passive Intraocular Pressure Sensors," Journal of Microelectromechanical Systems, Dec. 2008, pp. 1342-1351, vol. 17, No. 6.

Chu, et al., "Soft Contact-lens Sensor for Monitoring Tear Sugar as Novel Wearable Device of Body Sensor Network," http://www.ksi edu/seke/dms11/DMS/2_Kohji_Mitsubayashi.pdf, Last accessed Jul. 27, 2012, 4 pages.

"Contact Lenses: Look Into My Eyes," The Economist, Jun. 2, 2011, http://www.economist.com/node/18750624/print, Last accessed Mar. 13, 2012, 8 pages.

Haders, "New Controlled Release Technologies Broaden Opportunities for Ophthalmic Therapies," Drug Delivery Technology, Jul./Aug. 2009, pp. 48-53, vol. 8, No. 7.

Holloway, "Microsoft developing electronic contact lens to monitor blood sugar," Gizmag, Jan. 5, 2012, http://www.gizmag.com/microsoft-electronic-diabetic-contact-lens/20987/, Last accessed Mar. 13, 2012. 5 pages.

Huang, et al., "Wrinkling of Ultrathin Polymer Films," Mater. Res. Soc. Symp. Proc., 2006, 6 pages, vol. 924, Materials Research Society.

Hurst, "How contact lenses could help save your life," Mail Online, Apr. 19, 2010, http://www.dailymail.co.uk/health/article-1267345/How-contact-lenses-help-save-life.html, Last accessed Jul. 27, 2012.

Liao, et al., "A 3µW CMOS Glucose Sensor for Wireless Contact-Lens Tear Glucose Monitoring ," IEEE Journal of Solid-State Circuits, Jan. 2012, pp. 335-344, vol. 47, No. 1.

Liao, et al., "A 3-µW Wirelessly Powered CMOS Glucose Sensor for an Active Contact Lens," 2011 IEEE International Solid-State Circuits Conference, Session 2, Feb. 21, 2011, 3 pages.

Lingley, et al., "A Single-Pixel Wireless Contact Lens Display," Journal of Micromechanics and Microengineering, 2011, pp. 1-8.

Lingley, et al., "Multipurpose integrated active contact lenses," SPIE, 2009, 2 pages.

Liu, et al., "Miniature Amperometric Self-Powered Continuous Glucose Sensor with Linear Response," Analytical Chemistry, 2012, 7 pages.

Loncar, et al., "Design and Fabrication of Silicon Photonic Crystal Optical Waveguides," Journal of Lightwave Technology, Oct. 2000, pp. 1402-1411, vol. 18, No. 10.

Mursan, "Electro-responsive drug delivery from hydrogels," Journal of Controlled Release, 2003, pp. 1-17, vol. 92.

Pandey, et al., "A Fully Integrated RF-Powered Contact Lens With a Single Element Display," IEEE Transactions on Biomedical Circuits and Systems, Dec. 2010, pp. 454-461, vol. 4, No. 6.

Parviz, Babak A., "Augmented Reality in a Contact Lens," IEEE Spectrum, Sep. 2009, http://spectrum.ieee.org/biomedical/bionics/augmented-reality-in-a-contact-lens/0, Last accessed Mar. 14, 2012, 6 pages.

Selner, et al., "Novel Contact Lens Electrode Array for Multi-electrode Electroretinography (meERG)," IEEE, 2011, 2 pages.

Singh , et al., "Novel Approaches in Formulation and Drug Delivery using Contact Lenses," Journal of Basic and Clinical Pharmacy, May 2011, pp. 87-101, vol. 2, Issue 2.

Thomas, et al., "Functional Contact Lenses for Remote Health Monitoring in Developing Countries," IEEE Global Humanitarian Technology Conference, 2011, pp. 212-217, IEEE Computer Society.

Tweedie, et al., "Contact creep compliance of viscoelastic materials via nanoindentation," J. Mater. Res., Jun. 2006, pp. 1576-1589, vol. 21, No. 2, Materials Research Society.

Wall, K., "Active contact lens that lets you see like the Terminator patented," Feb. 10, 2012, http://www.patexia.com/feed/active-contact-lens-that-lets-you-see-like-the-terminator-patented-2407, Last accessed Mar. 28, 2012, 5 pages.

Zarbin, et al., "Nanotechnology in ophthalmology," Can J Ophthalmol, 2010, pp. 457-476, vol. 45, No. 5.

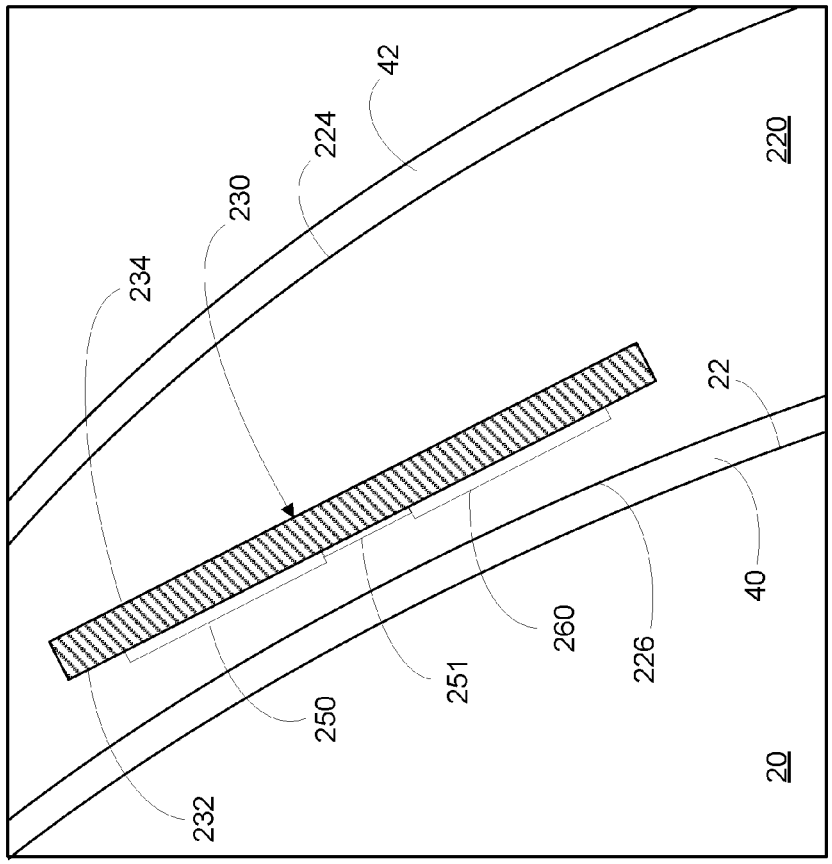
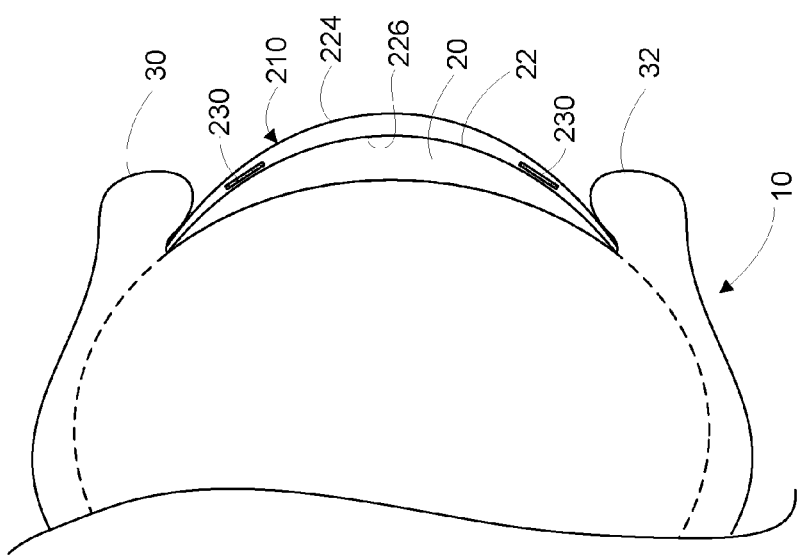
FIG. 2D
FIG. 2C

ENCAPSULATED ELECTRONICS

CROSS-REFERENCE TO RELATED APPLICATIONS

The present application is a continuation of U.S. patent application Ser. No. 14/518,986, filed Oct. 20, 2014, which is a continuation of U.S. patent application Ser. No. 13/741,725, filed Jan. 15, 2013, now U.S. Pat. No. 8,874,182. These applications are incorporated herein by reference.

BACKGROUND

Unless otherwise indicated herein, the materials described in this section are not prior art to the claims in this application and are not admitted to be prior art by inclusion in this section.

An electrochemical amperometric sensor measures a concentration of an analyte by measuring a current generated through electrochemical oxidation or reduction reactions of the analyte at a working electrode of the sensor. A reduction reaction occurs when electrons are transferred from the electrode to the analyte, whereas an oxidation reaction occurs when electrons are transferred from the analyte to the electrode. The direction of the electron transfer is dependent upon the electrical potentials applied to the working electrode. A counter electrode and/or reference electrode is used to complete a circuit with the working electrode and allow the generated current to flow. When the working electrode is appropriately biased, the output current can be proportional to the reaction rate, so as to provide a measure of the concentration of the analyte surrounding the working electrode.

In some examples, a reagent is localized proximate the working electrode to selectively react with a desired analyte. For example, glucose oxidase can be fixed near the working electrode to react with glucose and release hydrogen peroxide, which is then electrochemically detected by the working electrode to indicate the presence of glucose. Other enzymes and/or reagents can be used to detect other analytes.

SUMMARY

Some embodiments of the present disclosure provide an eye-mountable device including a transparent polymeric material, a substrate, an antenna, and a controller. The transparent polymeric material can have a concave surface and a convex surface. The concave surface can be configured to be removably mounted over a corneal surface and the convex surface can be configured to be compatible with eyelid motion when the concave surface is so mounted. The substrate can be at least partially embedded in the transparent polymeric material. The substrate can include an electrochemical sensor that includes a working electrode and a reference electrode. The substrate can also include an electronics module encapsulated within a bio-compatible material such that tear fluid permeating the transparent polymeric material is isolated from the electronics module by the bio-compatible material. The electronics module can includes an antenna and a controller. The controller can be electrically connected to the electrochemical sensor and the antenna. The controller can be configured to control the electrochemical sensor to obtain a sensor measurement related to a concentration of an analyte in a fluid to which the eye-mountable device is exposed and use the antenna to indicate the sensor measurement.

Some embodiments of the present disclosure provide a method including forming a sacrificial layer on a working substrate. The method can include forming a first layer of a bio-compatible material on the sacrificial layer. The method can include providing an electronics module on the first layer of the bio-compatible material. The method can include forming a second layer of the bio-compatible material to cover the electronics module. The method can include annealing the first and second layers of the bio-compatible material together to form an encapsulated structure. The encapsulated structure can include the electronics module fully enclosed within the bio-compatible material.

Some embodiments of the present disclosure provide a device prepared by a process. The process can include forming a sacrificial layer on a working substrate. The process can include forming a first layer of a bio-compatible material on the sacrificial layer. The process can include providing an electronics module on the first layer of the bio-compatible material. The process can include forming a second layer of the bio-compatible material to cover the electronics module. The process can include annealing the first and second layers of the bio-compatible material together to form an encapsulated structure. The encapsulated structure can include the electronics module fully enclosed within the bio-compatible material.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 2C is a side cross-section view of the example eye-mountable device shown in FIGS. 2A and 2B while mounted to a corneal surface of an eye.

FIG. 2D is a side cross-section view enhanced to show the tear film layers surrounding the surfaces of the example eye-mountable device when mounted as shown in FIG. 2C.

DETAILED DESCRIPTION

Figure 1:
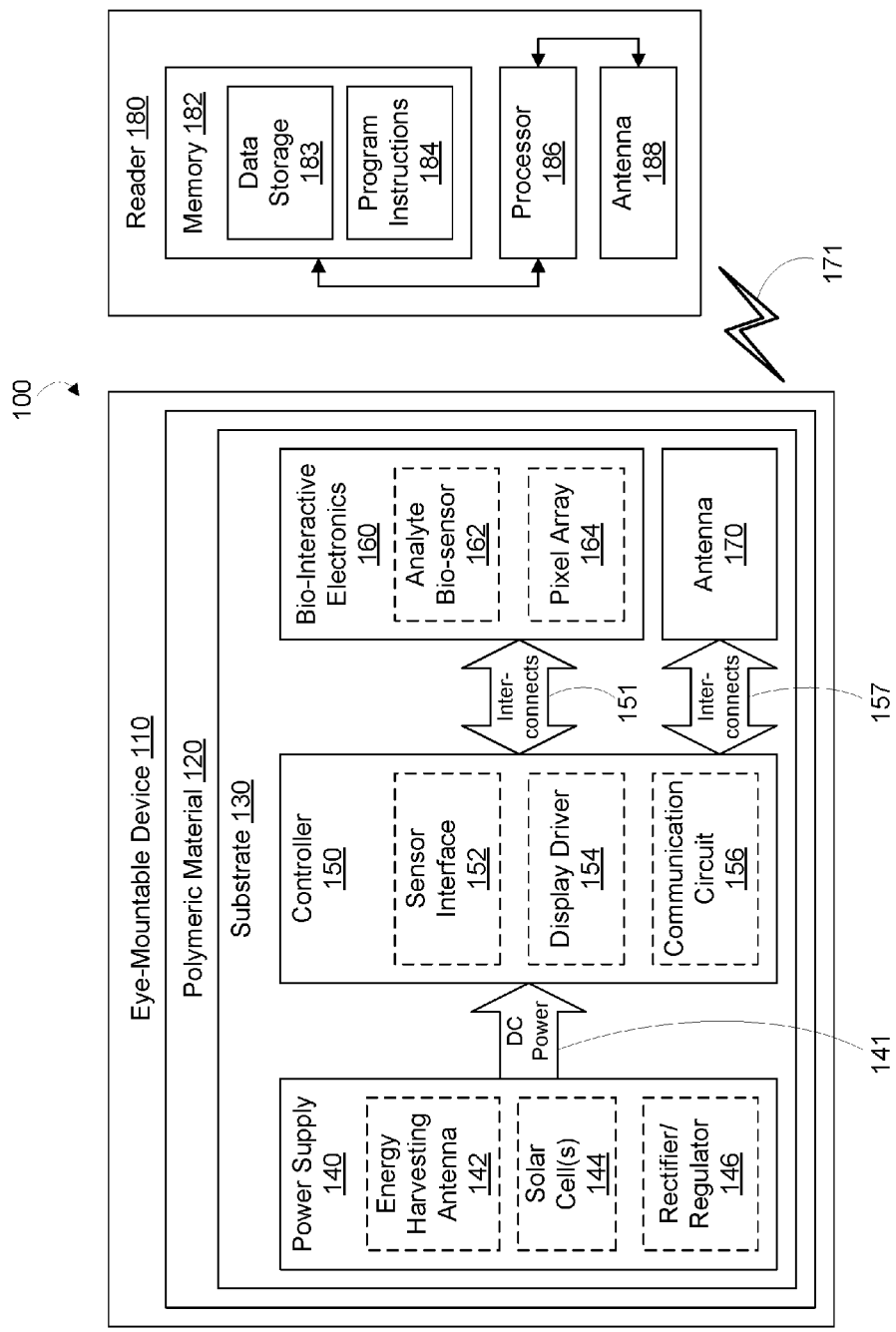
FIG. 1 is a block diagram of an example system that includes an eye-mountable device in wireless communication with an external reader.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

An ophthalmic sensing platform or implantable sensing platform can include a sensor, control electronics and an antenna all situated on a substrate embedded in a polymeric material. The polymeric material can be incorporated in an ophthalmic device, such as an eye-mountable device or an implantable medical device. The control electronics can operate the sensor to perform readings and can operate the antenna to wirelessly communicate the readings from the sensor to an external reader via the antenna.

In some examples, the polymeric material can be in the form of a round lens with a concave curvature configured to mount to a corneal surface of an eye. The substrate can be embedded near the periphery of the polymeric material to avoid interference with incident light received closer to the central region of the cornea. The sensor can be arranged on the substrate to face inward, toward the corneal surface, so as to generate clinically relevant readings from near the surface of the cornea and/or from tear fluid interposed between the contact lens and the corneal surface. In some examples, the sensor is entirely embedded within the contact lens material. For example, an electrochemical sensor that includes a working electrode and a reference electrode can be embedded in the lens material and situated such that the sensor electrodes are less than 10 micrometers from the polymeric surface configured to mount to the cornea. The sensor can generate an output signal indicative of a concentration of an analyte that diffuses through the lens material to the sensor electrodes.

The ophthalmic sensing platform can be powered via radiated energy harvested at the sensing platform. Power can be provided by light energizing photovoltaic cells included on the sensing platform. Additionally or alternatively, power can be provided by radio frequency energy harvested from the antenna. A rectifier and/or regulator can be incorporated with the control electronics to generate a stable DC voltage to power the sensing platform from the harvested energy. The antenna can be arranged as a loop of conductive material with leads connected to the control electronics. In some embodiments, such a loop antenna can also wirelessly communicate the sensor readings to an external reader by modifying the impedance of the loop antenna so as to modify backscatter radiation from the antenna.

Tear fluid contains a variety of inorganic electrolytes (e.g., $Ca^{2+}$, $Mg^{2+}$, $Cl^-$), organic components (e.g., glucose, lactate, proteins, lipids, etc.), and so on that can be used to diagnose health states. An ophthalmic sensing platform configured to measure one or more of these analytes can thus provide a convenient non-invasive platform useful in diagnosing and/or monitoring health states. For example, an ophthalmic sensing platform can be configured to sense glucose and can be used by diabetic individuals to measure/monitor their glucose levels.

In some embodiments of the present disclosure, an electronics module is entirely encapsulated by a bio-compatible material. The encapsulated electronics module may then be employed in applications involving contact with biological fluids without invoking a host response. An example technique for producing such an encapsulated electronics module is also disclosed herein. The electronics module can be encapsulated by building up a multi-layered structure, where the outer layers are formed of a bio-compatible material, and an inner layer includes the electronics module. Once the multi-layered structure is assembled, the respective outer layers of bio-compatible material can be annealed together to seal the edges around the electronics module. In some examples, the multi-layered structure can be assembled on a working substrate, such as a silicon wafer or another substantially flat surface suitable to be used as a microfabrication substrate. To prevent adhesion between the working substrate and the bio-compatible material during the annealing process, a sacrificial layer can be interposed between the working substrate and the bio-compatible material. The sacrificial layer can then be rinsed away, dissolved, or otherwise removed to release the multi-layered structure from the working substrate.

An example process for fabricating such a bio-compatible encapsulated electronics module is described. A first layer of bio-compatible material is formed by evaporation or another microfabrication technique. An electronics module is then provided on the first layer of bio-compatible material. A second layer of the bio-compatible material is then formed over the entire region spanned by the electronics module. Following the deposition of the second layer, the electronics module is situated between the first and second layers of bio-compatible material. For example, the top and bottom of the electronics module can be covered by the first and second layers of the bio-compatible material, respectively. The first and second layers of the bio-compatible material are deposited to span a greater coverage area than the electronics module such that areas where the second layer of the bio-compatible material is deposited directly on the first layer of the bio-compatible material surround the side edges of the electronics module.

The first and second layers are annealed together by placing the entire multi-layered structure in an oven heated to a temperature sufficient to anneal the bio-compatible material. Following the annealing, areas where the two layers of bio-compatible materials directly contacted one another, including the side edges of the electronics module, are sealed together by the annealed bond. The electronic components are thereby fully encapsulated by the bio-compatible material. In an example where the bio-compatible material is parylene C (e.g., dichlorodi-p-xylylene), the annealing temperature can be a temperature between 150 and 200 degrees Celsius.

In some examples, the layered structure is developed on a flat working substrate, such as a silicon wafer, and the annealing process is carried out while the layered structure is on the working substrate. In addition, a sacrificial layer can be coated on the working substrate prior to the deposition of the first layer of bio-compatible material. The sacrificial layer separates the bio-compatible material from the working substrate, and thereby prevents the bio-compatible material from adhering to the working substrate during the annealing process. The sacrificial layer can be a photoresist and/or a non-stick coating such as silane, soap, etc. Following the annealing process, the sacrificial layer may be dissolved by rinsing with a suitable solution to thereby release the bio-compatible encapsulated electronics from the working substrate. A rinsing solution may include acetone, isopropyl alcohol, and/or water. Generally, the rinsing solution is selected to dissolve the sacrificial layer without affecting the bio-compatible material.

In some examples, the layered structure is developed on a working substrate that is not coated with a sacrificial layer. For example, the first layer of bio-compatible material can be applied directly on a working substrate, such as a clean silicon wafer. Electronics to be encapsulated can then be provided on the first layer of bio-compatible material and a second layer of bio-compatible material can be formed over the electronics. Following the annealing, the bio-compatible encapsulated electronics can be peeled away from the working substrate. In some examples, the bio-compatible material may form a conformal coating around the working substrate, such as where the layers of bio-compatible material are formed by an evaporation process. The bio-compatible encapsulated electronics may be peeled away from the working substrate after the portions of the bio-compatible material that wrap around the working substrate are trimmed away (e.g., by etching the annealed layers of bio-compatible material to create an encapsulated electronics structure with a desired shape).

In some examples, the layered structure can be formed into a desired shape following the annealing. For example, where the layered structure is developed on a working substrate, oxygen plasma can be used to etch the layered structure prior to rinsing the encapsulated electronics module from the working substrate. For example, the layered structure can be etched to create a ring-shaped structure configured to be embedded around the perimeter of an eye-mountable device made of a suitable polymeric material.

The electronics module can include a power harvesting system for harvesting energy from incident radiation (e.g., a radio frequency antenna for inductively harvesting energy from incident radio frequency radiation and/or a photovoltaic cell for harvesting energy from incident visible, infrared, and/or ultraviolet light). The encapsulated electronics module can thereby be powered wirelessly.

In one example application, an encapsulated bio-interactive electronics module is embedded in an eye-mountable device. The eye-mountable device is configured to rest on a corneal surface of an eye. The eye-mountable device may be formed of a polymeric material, such as a hydrogel material similar to that employed for ophthalmic contact lenses. Some examples of bio-interactive electronics that may be included in the eye-mountable device include biosensors for monitoring tear film analyte concentrations and/or near-eye displays for providing visual cues to the wearer. Thus, the bio-interactive electronics may receive information from the wearer (e.g., a bio-sensor that captures analyte concentration information) and/or convey information to the wearer (e.g., a near-eye display that communicates information to the wearer). The bio-interactive electronics can be powered by harvested energy and may not include a significant on-board power supply and/or power storage. For example, the bio-interactive electronics may be powered via an integrated antenna configured to inductively harvest energy from incident radio frequency radiation and/or via a photovoltaic cell configured to harvest energy from incident light. The bio-interactive electronics module is encapsulated (sealed) within a bio-compatible material by two layers of the bio-compatible material annealed together to seal the respective overlapping edges. The bio-compatible material can be shaped as a flattened ring situated around the periphery of the eye-mountable device so as to avoid interference with light transmission to the light-receptive pupil near the central portion of the eye while the eye-mountable device is mounted over a corneal surface.

Thus, the bio-interactive electronics module may be a sensing platform with a sensor, control electronics and an antenna all encapsulated within a bio-compatible substrate. In operation, the control electronics operate the sensor to perform readings and operate the antenna to wirelessly communicate the readings from the sensor to an external reader via the antenna. In an example where the sensor is an electrochemical sensor, the control electronics can be configured to apply an operating voltage to the sensor electrodes sufficient to generate an amperometric current, measure the amperometric current, and use the antenna to communicate the measured amperometric current to an external reader.

II. Example Ophthalmic Electronics Platform

FIG. 1 is a block diagram of a system 100 that includes an eye-mountable device 110 in wireless communication with an external reader 180. The exposed regions of the eye-mountable device 110 are made of a polymeric material 120 formed to be contact-mounted to a corneal surface of an eye. A substrate 130 is embedded in the polymeric material 120 to provide a mounting surface for a power supply 140, a controller 150, bio-interactive electronics 160, and a communication antenna 170. The bio-interactive electronics 160 are operated by the controller 150. The power supply 140 supplies operating voltages to the controller 150 and/or the bio-interactive electronics 160. The antenna 170 is operated by the controller 150 to communicate information to and/or from the eye-mountable device 110. The antenna 170, the controller 150, the power supply 140, and the bio-interactive electronics 160 can all be situated on the embedded substrate 130. Because the eye-mountable device 110 includes electronics and is configured to be contact-mounted to an eye, it is also referred to herein as an ophthalmic electronics platform.

To facilitate contact-mounting, the polymeric material 120 can have a concave surface configured to adhere ("mount") to a moistened corneal surface (e.g., by capillary forces with a tear film coating the corneal surface). Additionally or alternatively, the eye-mountable device 110 can be adhered by a vacuum force between the corneal surface and the polymeric material due to the concave curvature. While mounted with the concave surface against the eye, the outward-facing surface of the polymeric material 120 can have a convex curvature that is formed to not interfere with eye-lid motion while the eye-mountable device 110 is mounted to the eye. For example, the polymeric material 120 can be a substantially transparent curved polymeric disk shaped similarly to a contact lens.

The polymeric material 120 can include one or more biocompatible materials, such as those employed for use in contact lenses or other ophthalmic applications involving direct contact with the corneal surface. The polymeric material 120 can optionally be formed in part from such biocompatible materials or can include an outer coating with such biocompatible materials. The polymeric material 120 can include materials configured to moisturize the corneal surface, such as hydrogels and the like. In some embodiments, the polymeric material 120 can be a deformable ("non-rigid") material to enhance wearer comfort. In some embodiments, the polymeric material 120 can be shaped to provide a predetermined, vision-correcting optical power, such as can be provided by a contact lens.

The substrate 130 includes one or more surfaces suitable for mounting the bio-interactive electronics 160, the controller 150, the power supply 140, and the antenna 170. The substrate 130 can be employed both as a mounting platform for chip-based circuitry (e.g., by flip-chip mounting to connection pads) and/or as a platform for patterning conductive materials (e.g., gold, platinum, palladium, titanium, copper, aluminum, silver, metals, other conductive materials, combinations of these, etc.) to create electrodes, interconnects, connection pads, antennae, etc. In some embodiments, substantially transparent conductive materials (e.g., indium tin oxide) can be patterned on the substrate 130 to form circuitry, electrodes, etc. For example, the antenna 170 can be formed by forming a pattern of gold or another conductive material on the substrate 130 by deposition, photolithography, electroplating, etc. Similarly, interconnects 151, 157 between the controller 150 and the bio-interactive electronics 160, and between the controller 150 and the antenna 170, respectively, can be formed by depositing suitable patterns of conductive materials on the substrate 130. A combination of microfabrication techniques including, without limitation, the use of photoresists, masks, deposition techniques, and/or plating techniques can be employed to pattern materials on the substrate 130. The substrate 130 can be a relatively rigid material, such as polyethylene terephthalate ("PET") or another material configured to structurally support the circuitry and/or chip-based electronics within the polymeric material 120. The eye-mountable device 110 can alternatively be arranged with a group of unconnected substrates rather than a single substrate. For example, the controller 150 and a bio-sensor or other bio-interactive electronic component can be mounted to one substrate, while the antenna 170 is mounted to another substrate and the two can be electrically connected via the interconnects 157.

In some embodiments, the bio-interactive electronics 160 (and the substrate 130) can be positioned away from the center of the eye-mountable device 110 and thereby avoid interference with light transmission to the central, light-sensitive region of the eye. For example, where the eye-mountable device 110 is shaped as a concave-curved disk, the substrate 130 can be embedded around the periphery (e.g., near the outer circumference) of the disk. In some embodiments, however, the bio-interactive electronics 160 (and the substrate 130) can be positioned in or near the central region of the eye-mountable device 110. Additionally or alternatively, the bio-interactive electronics 160 and/or substrate 130 can be substantially transparent to incoming visible light to mitigate interference with light transmission to the eye. Moreover, in some embodiments, the bio-interactive electronics 160 can include a pixel array 164 that emits and/or transmits light to be received by the eye according to display instructions. Thus, the bio-interactive electronics 160 can optionally be positioned in the center of the eye-mountable device so as to generate perceivable visual cues to a wearer of the eye-mountable device 110, such as by displaying information (e.g., characters, symbols, flashing patterns, etc.) on the pixel array 164.

The substrate 130 can be shaped as a flattened ring with a radial width dimension sufficient to provide a mounting platform for the embedded electronics components. The substrate 130 can have a thickness sufficiently small to allow the substrate 130 to be embedded in the polymeric material 120 without influencing the profile of the eye-mountable device 110. The substrate 130 can have a thickness sufficiently large to provide structural stability suitable for supporting the electronics mounted thereon. For example, the substrate 130 can be shaped as a ring with a diameter of about 10 millimeters, a radial width of about 1 millimeter (e.g., an outer radius 1 millimeter larger than an inner radius), and a thickness of about 50 micrometers. The substrate 130 can optionally be aligned with the curvature of the eye-mounting surface of the eye-mountable device 110 (e.g., convex surface). For example, the substrate 130 can be shaped along the surface of an imaginary cone between two circular segments that define an inner radius and an outer radius. In such an example, the surface of the substrate 130 along the surface of the imaginary cone defines an inclined surface that is approximately aligned with the curvature of the eye mounting surface at that radius.

The power supply 140 is configured to harvest ambient energy to power the controller 150 and bio-interactive electronics 160. For example, a radio-frequency energy-harvesting antenna 142 can capture energy from incident radio radiation. Additionally or alternatively, solar cell(s) 144 ("photovoltaic cells") can capture energy from incoming ultraviolet, visible, and/or infrared radiation. Furthermore, an inertial power scavenging system can be included to capture energy from ambient vibrations. The energy harvesting antenna 142 can optionally be a dual-purpose antenna that is also used to communicate information to the external reader 180. That is, the functions of the communication antenna 170 and the energy harvesting antenna 142 can be accomplished with the same physical antenna.

A rectifier/regulator 146 can be used to condition the captured energy to a stable DC supply voltage 141 that is supplied to the controller 150. For example, the energy harvesting antenna 142 can receive incident radio frequency radiation. Varying electrical signals on the leads of the antenna 142 are output to the rectifier/regulator 146. The rectifier/regulator 146 rectifies the varying electrical signals to a DC voltage and regulates the rectified DC voltage to a level suitable for operating the controller 150. Additionally or alternatively, output voltage from the solar cell(s) 144 can be regulated to a level suitable for operating the controller 150. The rectifier/regulator 146 can include one or more energy storage devices to mitigate high frequency variations in the ambient energy gathering antenna 142 and/or solar cell(s) 144. For example, one or more energy storage devices (e.g., a capacitor, an inductor, etc.) can be connected in parallel across the outputs of the rectifier 146 to regulate the DC supply voltage 141 and configured to function as a low-pass filter.

The controller 150 is turned on when the DC supply voltage 141 is provided to the controller 150, and the logic in the controller 150 operates the bio-interactive electronics 160 and the antenna 170. The controller 150 can include logic circuitry configured to operate the bio-interactive electronics 160 so as to interact with a biological environment of the eye-mountable device 110. The interaction could involve the use of one or more components, such an analyte bio-sensor 162, in bio-interactive electronics 160 to obtain input from the biological environment. Additionally or alternatively, the interaction could involve the use of one or more components, such as pixel array 164, to provide an output to the biological environment.

In one example, the controller 150 includes a sensor interface module 152 that is configured to operate analyte bio-sensor 162. The analyte bio-sensor 162 can be, for example, an amperometric electrochemical sensor that includes a working electrode and a reference electrode. A voltage can be applied between the working and reference electrodes to cause an analyte to undergo an electrochemical reaction (e.g., a reduction and/or oxidation reaction) at the working electrode. The electrochemical reaction can generate an amperometric current that can be measured through the working electrode. The amperometric current can be dependent on the analyte concentration. Thus, the amount of the amperometric current that is measured through the working electrode can provide an indication of analyte concentration. In some embodiments, the sensor interface module 152 can be a potentiostat configured to apply a voltage difference between working and reference electrodes while measuring a current through the working electrode.

In some instances, a reagent can also be included to sensitize the electrochemical sensor to one or more desired analytes. For example, a layer of glucose oxidase ("GOD") proximal to the working electrode can catalyze glucose oxidation to generate hydrogen peroxide ($H_2O_2$). The hydrogen peroxide can then be electro-oxidized at the working electrode, which releases electrons to the working electrode, resulting in an amperometric current that can be measured through the working electrode.

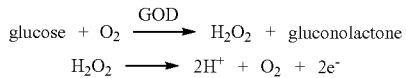

$$\text{glucose} + O_2 \xrightarrow{\text{GOD}} H_2O_2 + \text{gluconolactone}$$
$$H_2O_2 \longrightarrow 2H^+ + O_2 + 2e^-$$

The current generated by either reduction or oxidation reactions is approximately proportionate to the reaction rate. Further, the reaction rate is dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate is approximately proportionate to the concentration of the analyte molecules. The current measured through the working electrode thus provides an indication of the analyte concentration.

The controller 150 can optionally include a display driver module 154 for operating a pixel array 164. The pixel array 164 can be an array of separately programmable light transmitting, light reflecting, and/or light emitting pixels arranged in rows and columns. The individual pixel circuits can optionally include liquid crystal technologies, micro-electromechanical technologies, emissive diode technologies, etc. to selectively transmit, reflect, and/or emit light according to information from the display driver module 154. Such a pixel array 164 can also optionally include more than one color of pixels (e.g., red, green, and blue pixels) to render visual content in color. The display driver module 154 can include, for example, one or more data lines providing programming information to the separately programmed pixels in the pixel array 164 and one or more addressing lines for setting groups of pixels to receive such programming information. Such a pixel array 164 situated on the eye can also include one or more lenses to direct light from the pixel array to a focal plane perceivable by the eye.

The controller 150 can also include a communication circuit 156 for sending and/or receiving information via the antenna 170. The communication circuit 156 can optionally include one or more oscillators, mixers, frequency injectors, etc. to modulate and/or demodulate information on a carrier frequency to be transmitted and/or received by the antenna 170. In some examples, the eye-mountable device 110 is configured to indicate an output from a bio-sensor by modulating an impedance of the antenna 170 in a manner that is perceivable by the external reader 180. For example, the communication circuit 156 can cause variations in the amplitude, phase, and/or frequency of backscatter radiation from the antenna 170, and such variations can be detected by the reader 180.

The controller 150 is connected to the bio-interactive electronics 160 via interconnects 151. For example, where the controller 150 includes logic elements implemented in an integrated circuit to form the sensor interface module 152 and/or display driver module 154, a patterned conductive material (e.g., gold, platinum, palladium, titanium, copper, aluminum, silver, metals, combinations of these, etc.) can connect a terminal on the chip to the bio-interactive electronics 160. Similarly, the controller 150 is connected to the antenna 170 via interconnects 157.

It is noted that the block diagram shown in FIG. 1 is described in connection with functional modules for convenience in description. However, embodiments of the eye-mountable device 110 can be arranged with one or more of the functional modules ("sub-systems") implemented in a single chip, integrated circuit, and/or physical component. For example, while the rectifier/regulator 146 is illustrated in the power supply block 140, the rectifier/regulator 146 can be implemented in a chip that also includes the logic elements of the controller 150 and/or other features of the embedded electronics in the eye-mountable device 110. Thus, the DC supply voltage 141 that is provided to the controller 150 from the power supply 140 can be a supply voltage that is provided to components on a chip by rectifier and/or regulator components located on the same chip. That is, the functional blocks in FIG. 1 shown as the power supply block 140 and controller block 150 need not be implemented as physically separated modules. Moreover, one or more of the functional modules described in FIG. 1 can be implemented by separately packaged chips electrically connected to one another.

Additionally or alternatively, the energy harvesting antenna 142 and the communication antenna 170 can be implemented with the same physical antenna. For example, a loop antenna can both harvest incident radiation for power generation and communicate information via backscatter radiation.

The external reader 180 includes an antenna 188 (or group of more than one antennae) to send and receive wireless signals 171 to and from the eye-mountable device 110. The external reader 180 also includes a computing system with a processor 186 in communication with a memory 182. The memory 182 is a non-transitory computer-readable medium that can include, without limitation, magnetic disks, optical disks, organic memory, and/or any other volatile (e.g. RAM) or non-volatile (e.g. ROM) storage system readable by the processor 186. The memory 182 can include a data storage 183 to store indications of data, such as sensor readings (e.g., from the analyte bio-sensor 162), program settings (e.g., to adjust behavior of the eye-mountable device 110 and/or external reader 180), etc. The memory 182 can also include program instructions 184 for execution by the processor 186 to cause the external reader 180 to perform processes specified by the instructions 184. For example, the program instructions 184 can cause external reader 180 to provide a user interface that allows for retrieving information communicated from the eye-mountable device 110 (e.g., sensor outputs from the analyte bio-sensor 162). The external reader 180 can also include one or more hardware components for operating the antenna 188 to send and receive the wireless signals 171 to and from the eye-mountable device 110. For example, oscillators, frequency injectors, encoders, decoders, amplifiers, filters, etc. can drive the antenna 188 according to instructions from the processor 186.

The external reader 180 can be a smart phone, digital assistant, or other portable computing device with wireless connectivity sufficient to provide the wireless communication link 171. The external reader 180 can also be implemented as an antenna module that can be plugged in to a portable computing device, such as in an example where the communication link 171 operates at carrier frequencies not commonly employed in portable computing devices. In some instances, the external reader 180 is a special-purpose device configured to be worn relatively near a wearer's eye to allow the wireless communication link 171 to operate with a low power budget. For example, the external reader 180 can be integrated in a piece of jewelry such as a necklace, earring, etc. or integrated in an article of clothing worn near the head, such as a hat, headband, etc.

In an example where the eye-mountable device 110 includes an analyte bio-sensor 162, the system 100 can be operated to monitor the analyte concentration in tear film on the surface of the eye. Thus, the eye-mountable device 110 can be configured as a platform for an ophthalmic analyte bio-sensor. The tear film is an aqueous layer secreted from the lacrimal gland to coat the eye. The tear film is in contact with the blood supply through capillaries in the structure of the eye and includes many biomarkers found in blood that are analyzed to characterize a person's health condition(s). For example, the tear film includes glucose, calcium, sodium, cholesterol, potassium, other biomarkers, etc. The biomarker concentrations in the tear film can be systematically different than the corresponding concentrations of the biomarkers in the blood, but a relationship between the two concentration levels can be established to map tear film biomarker concentration values to blood concentration levels. For example, the tear film concentration of glucose can be established (e.g., empirically determined) to be approximately one tenth the corresponding blood glucose concentration. Although another ratio relationship and/or a non-ratio relationship may be used. Thus, measuring tear film analyte concentration levels provides a non-invasive technique for monitoring biomarker levels in comparison to blood sampling techniques performed by lancing a volume of blood to be analyzed outside a person's body. Moreover, the ophthalmic analyte bio-sensor platform disclosed here can be operated substantially continuously to enable real time monitoring of analyte concentrations.

To perform a reading with the system 100 configured as a tear film analyte monitor, the external reader 180 can emit radio frequency radiation 171 that is harvested to power the eye-mountable device 110 via the power supply 140. Radio frequency electrical signals captured by the energy harvesting antenna 142 (and/or the communication antenna 170) are rectified and/or regulated in the rectifier/regulator 146 and a regulated DC supply voltage 147 is provided to the controller 150. The radio frequency radiation 171 thus turns on the electronic components within the eye-mountable device 110. Once turned on, the controller 150 operates the analyte bio-sensor 162 to measure an analyte concentration level. For example, the sensor interface module 152 can apply a voltage between a working electrode and a reference electrode in the analyte bio-sensor 162. The applied voltage can be sufficient to cause the analyte to undergo an electrochemical reaction at the working electrode and thereby generate an amperometric current that can be measured through the working electrode. The measured amperometric current can provide the sensor reading ("result") indicative of the analyte concentration. The controller 150 can operate the antenna 170 to communicate the sensor reading back to the external reader 180 (e.g., via the communication circuit 156). The sensor reading can be communicated by, for example, modulating an impedance of the communication antenna 170 such that the modulation in impedance is detected by the external reader 180. The modulation in antenna impedance can be detected by, for example, backscatter radiation from the antenna 170.

In some embodiments, the system 100 can operate to non-continuously ("intermittently") supply energy to the eye-mountable device 110 to power the controller 150 and electronics 160. For example, radio frequency radiation 171 can be supplied to power the eye-mountable device 110 long enough to carry out a tear film analyte concentration measurement and communicate the results. For example, the supplied radio frequency radiation can provide sufficient power to apply a potential between a working electrode and a reference electrode sufficient to induce electrochemical reactions at the working electrode, measure the resulting amperometric current, and modulate the antenna impedance to adjust the backscatter radiation in a manner indicative of the measured amperometric current. In such an example, the supplied radio frequency radiation 171 can be considered an interrogation signal from the external reader 180 to the eye-mountable device 110 to request a measurement. By periodically interrogating the eye-mountable device 110 (e.g., by supplying radio frequency radiation 171 to temporarily turn the device on) and storing the sensor results (e.g., via the data storage 183), the external reader 180 can accumulate a set of analyte concentration measurements over time without continuously powering the eye-mountable device 110.

Figure 2A:
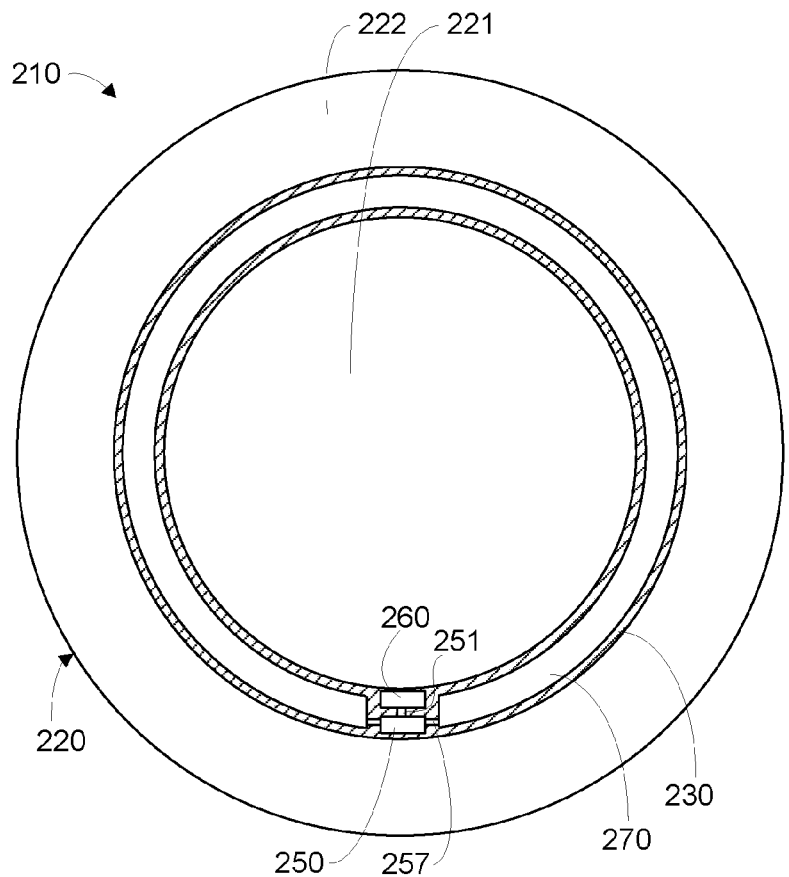
FIG. 2A is a bottom view of an example eye-mountable device.
Figure 2B:
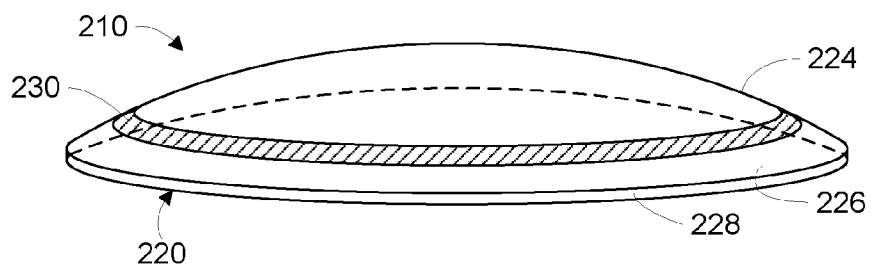
FIG. 2B is a side view of the example eye-mountable device shown in FIG. 2A.

FIG. 2A is a bottom view of an example eye-mountable electronic device 210 (or ophthalmic electronics platform). FIG. 2B is an aspect view of the example eye-mountable electronic device shown in FIG. 2A. It is noted that relative dimensions in FIGS. 2A and 2B are not necessarily to scale, but have been rendered for purposes of explanation only in describing the arrangement of the example eye-mountable electronic device 210. The eye-mountable device 210 is formed of a polymeric material 220 shaped as a curved disk. The polymeric material 220 can be a substantially transparent material to allow incident light to be transmitted to the eye while the eye-mountable device 210 is mounted to the eye. The polymeric material 220 can be a biocompatible material similar to those employed to form vision correction and/or cosmetic contact lenses in optometry, such as polyethylene terephthalate ("PET"), polymethyl methacrylate ("PMMA"), polyhydroxyethylmethacrylate ("polyHEMA"), silicone hydrogels, combinations of these, etc. The polymeric material 220 can be formed with one side having a concave surface 226 suitable to fit over a corneal surface of an eye. The opposite side of the disk can have a convex surface 224 that does not interfere with eyelid motion while the eye-mountable device 210 is mounted to the eye. A circular outer side edge 228 connects the concave surface 224 and convex surface 226.

The eye-mountable device 210 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 210 can be selected according to the size and/or shape of the corneal surface of the wearer's eye.

The polymeric material 220 can be formed with a curved shape in a variety of ways. For example, techniques similar to those employed to form vision-correction contact lenses, such as heat molding, injection molding, spin casting, etc.

can be employed to form the polymeric material 220. While the eye-mountable device 210 is mounted in an eye, the convex surface 224 faces outward to the ambient environment while the concave surface 226 faces inward, toward the corneal surface. The convex surface 224 can therefore be considered an outer, top surface of the eye-mountable device 210 whereas the concave surface 226 can be considered an inner, bottom surface. The "bottom" view shown in FIG. 2A is facing the concave surface 226. From the bottom view shown in FIG. 2A, the outer periphery 222, near the outer circumference of the curved disk is curved to extend out of the page, whereas the central region 221, near the center of the disk is curved to extend into the page.

A substrate 230 is embedded in the polymeric material 220. The substrate 230 can be embedded to be situated along the outer periphery 222 of the polymeric material 220, away from the central region 221. The substrate 230 does not interfere with vision because it is too close to the eye to be in focus and is positioned away from the central region 221 where incident light is transmitted to the eye-sensing portions of the eye. Moreover, the substrate 230 can be formed of a transparent material to further mitigate effects on visual perception.

The substrate 230 can be shaped as a flat, circular ring (e.g., a disk with a centered hole). The flat surface of the substrate 230 (e.g., along the radial width) is a platform for mounting electronics such as chips (e.g., via flip-chip mounting) and for patterning conductive materials (e.g., via microfabrication techniques such as photolithography, deposition, plating, etc.) to form electrodes, antenna(e), and/or interconnections. The substrate 230 and the polymeric material 220 can be approximately cylindrically symmetric about a common central axis. The substrate 230 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only, and in no way limit the present disclosure. The substrate 230 can be implemented in a variety of different form factors, similar to the discussion of the substrate 130 in connection with FIG. 1 above.

A loop antenna 270, controller 250, and bio-interactive electronics 260 are disposed on the embedded substrate 230. The controller 250 can be a chip including logic elements configured to operate the bio-interactive electronics 260 and the loop antenna 270. The controller 250 is electrically connected to the loop antenna 270 by interconnects 257 also situated on the substrate 230. Similarly, the controller 250 is electrically connected to the bio-interactive electronics 260 by an interconnect 251. The interconnects 251, 257, the loop antenna 270, and any conductive electrodes (e.g., for an electrochemical analyte bio-sensor, etc.) can be formed from conductive materials patterned on the substrate 230 by a process for precisely patterning such materials, such as deposition, photolithography, etc. The conductive materials patterned on the substrate 230 can be, for example, gold, platinum, palladium, titanium, carbon, aluminum, copper, silver, silver-chloride, conductors formed from noble materials, metals, combinations of these, etc.

As shown in FIG. 2A, which is a view facing the concave surface 226 of the eye-mountable device 210, the bio-interactive electronics module 260 is mounted to a side of the substrate 230 facing the concave surface 226. Where the bio-interactive electronics module 260 includes an analyte bio-sensor, for example, mounting such a bio-sensor on the substrate 230 to be close to the concave surface 226 allows the bio-sensor to sense analyte concentrations in tear film near the surface of the eye. However, the electronics, electrodes, etc. situated on the substrate 230 can be mounted to either the "inward" facing side (e.g., situated closest to the concave surface 226) or the "outward" facing side (e.g., situated closest to the convex surface 224). Moreover, in some embodiments, some electronic components can be mounted on one side of the substrate 230, while other electronic components are mounted to the opposing side, and connections between the two can be made through conductive materials passing through the substrate 230.

The loop antenna 270 is a layer of conductive material patterned along the flat surface of the substrate to form a flat conductive ring. In some instances, the loop antenna 270 can be formed without making a complete loop. For instances, the antenna 270 can have a cutout to allow room for the controller 250 and bio-interactive electronics 260, as illustrated in FIG. 2A. However, the loop antenna 270 can also be arranged as a continuous strip of conductive material that wraps entirely around the flat surface of the substrate 230 one or more times. For example, a strip of conductive material with multiple windings can be patterned on the side of the substrate 230 opposite the controller 250 and bio-interactive electronics 260. Interconnects between the ends of such a wound antenna (e.g., the antenna leads) can then be passed through the substrate 230 to the controller 250.

FIG. 2C is a side cross-section view of the example eye-mountable electronic device 210 while mounted to a corneal surface 22 of an eye 10. FIG. 2D is a close-in side cross-section view enhanced to show the tear film layers 40, 42 surrounding the exposed surfaces 224, 226 of the example eye-mountable device 210. It is noted that relative dimensions in FIGS. 2C and 2D are not necessarily to scale, but have been rendered for purposes of explanation only in describing the arrangement of the example eye-mountable electronic device 210. For example, the total thickness of the eye-mountable device can be about 200 micrometers, while the thickness of the tear film layers 40, 42 can each be about 10 micrometers, although this ratio may not be reflected in the drawings. Some aspects are exaggerated to allow for illustration and facilitate explanation.

The eye 10 includes a cornea 20 that is covered by bringing the upper eyelid 30 and lower eyelid 32 together over the top of the eye 10. Incident light is received by the eye 10 through the cornea 20, where light is optically directed to light sensing elements of the eye 10 (e.g., rods and cones, etc.) to stimulate visual perception. The motion of the eyelids 30, 32 distributes a tear film across the exposed corneal surface 22 of the eye 10. The tear film is an aqueous solution secreted by the lacrimal gland to protect and lubricate the eye 10. When the eye-mountable device 210 is mounted in the eye 10, the tear film coats both the concave and convex surfaces 224, 226 with an inner layer 40 (along the concave surface 226) and an outer layer 42 (along the convex layer 224). The tear film layers 40, 42 can be about 10 micrometers in thickness and together account for about 10 microliters.

The tear film layers 40, 42 are distributed across the corneal surface 22 and/or the convex surface 224 by motion of the eyelids 30, 32. For example, the eyelids 30, 32 raise and lower, respectively, to spread a small volume of tear film across the corneal surface 22 and/or the convex surface 224 of the eye-mountable device 210. The tear film layer 40 on the corneal surface 22 also facilitates mounting the eye-mountable device 210 by capillary forces between the concave surface 226 and the corneal surface 22. In some embodiments, the eye-mountable device 210 can also be held over the eye in part by vacuum forces against corneal surface 22 due to the concave curvature of the eye-facing concave surface 226.

As shown in the cross-sectional views in FIGS. 2C and 2D, the substrate 230 can be inclined such that the flat mounting surfaces of the substrate 230 are approximately parallel to the adjacent portion of the concave surface 226. As described above, the substrate 230 is a flattened ring with an inward-facing surface 232 (closer to the concave surface 226 of the polymeric material 220) and an outward-facing surface 234 (closer to the convex surface 224). The substrate 230 can have electronic components and/or patterned conductive materials mounted to either or both mounting surfaces 232, 234. As shown in FIG. 2D, the bio-interactive electronics 260, controller 250, and conductive interconnect 251 are mounted on the inward-facing surface 232 such that the bio-interactive electronics 260 are relatively closer in proximity to the corneal surface 22 than if they were mounted on the outward-facing surface 234.

III. An Ophthalmic Electrochemical Analyte Sensor

Figure 3:
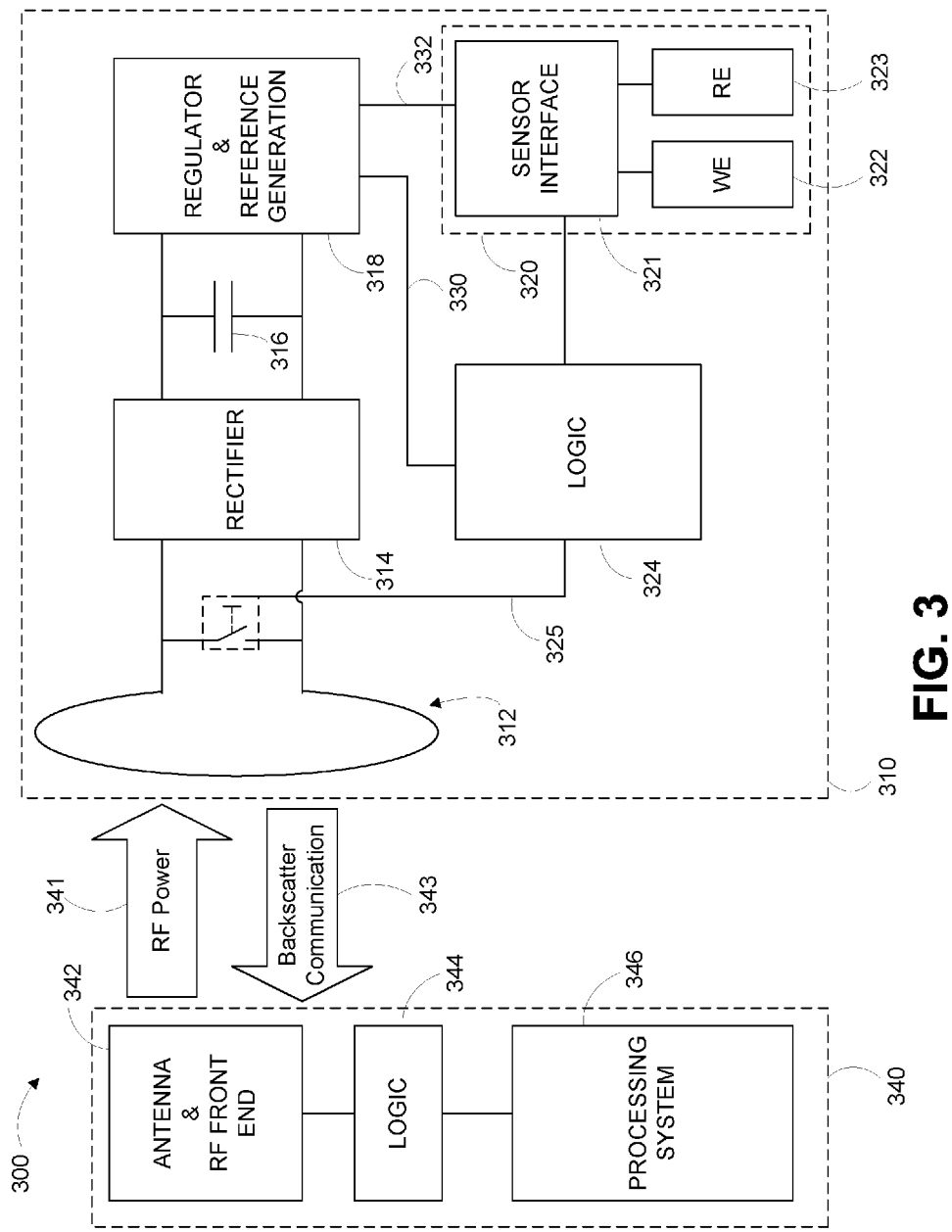
FIG. 3 is a functional block diagram of an example system for electrochemically measuring a tear film analyte concentration.

FIG. 3 is a functional block diagram of a system 300 for electrochemically measuring a tear film analyte concentration. The system 300 includes an eye-mountable device 310 with embedded electronic components powered by an external reader 340. The eye-mountable device 310 includes an antenna 312 for capturing radio frequency radiation 341 from the external reader 340. The eye-mountable device 310 includes a rectifier 314, an energy storage 316, and regulator 318 for generating power supply voltages 330, 332 to operate the embedded electronics. The eye-mountable device 310 includes an electrochemical sensor 320 with a working electrode 322 and a reference electrode 323 driven by a sensor interface 321. The eye-mountable device 310 includes hardware logic 324 for communicating results from the sensor 320 to the external reader 340 by modulating the impedance of the antenna 312. An impedance modulator 325 (shown symbolically as a switch in FIG. 3) can be used to modulate the antenna impedance according to instructions from the hardware logic 324. Similar to the eye-mountable devices 110, 210 discussed above in connection with FIGS. 1 and 2, the eye-mountable device 310 can include a mounting substrate embedded within a polymeric material configured to be mounted to an eye.

The electrochemical sensor 320 can be situated on a mounting surface of such a substrate proximate the surface of the eye (e.g., corresponding to the bio-interactive electronics 260 on the inward-facing side 232 of the substrate 230) to measure analyte concentration in a tear film layer interposed between the eye-mountable device 310 and the eye (e.g., the inner tear film layer 40 between the eye-mountable device 210 and the corneal surface 22). In some embodiments, however, an electrochemical sensor can be situated on a mounting surface of such a substrate distal the surface of the eye (e.g., corresponding to the outward-facing side 234 of the substrate 230) to measure analyte concentration in a tear film layer coating the exposed surface of the eye-mountable device 310 (e.g., the outer tear film layer 42 interposed between the convex surface 224 of the polymeric material 210 and the atmosphere and/or closed eyelids).

With reference to FIG. 3, the electrochemical sensor 320 measures analyte concentration by applying a voltage between the electrodes 322, 323 that is sufficient to cause products of the analyte catalyzed by the reagent to electrochemically react (e.g., a reduction and/or oxidization reaction) at the working electrode 322. The electrochemical reactions at the working electrode 322 generate an amperometric current that can be measured at the working electrode 322. The sensor interface 321 can, for example, apply a reduction voltage between the working electrode 322 and the reference electrode 323 to reduce products from the reagent-catalyzed analyte at the working electrode 322. Additionally or alternatively, the sensor interface 321 can apply an oxidization voltage between the working electrode 322 and the reference electrode 323 to oxidize the products from the reagent-catalyzed analyte at the working electrode 322. The sensor interface 321 measures the amperometric current and provides an output to the hardware logic 324. The sensor interface 321 can include, for example, a potentiostat connected to both electrodes 322, 323 to simultaneously apply a voltage between the working electrode 322 and the reference electrode 323 and measure the resulting amperometric current through the working electrode 322.

The rectifier 314, energy storage 316, and voltage regulator 318 operate to harvest energy from received radio frequency radiation 341. The radio frequency radiation 341 causes radio frequency electrical signals on leads of the antenna 312. The rectifier 314 is connected to the antenna leads and converts the radio frequency electrical signals to a DC voltage. The energy storage 316 (e.g., capacitor) is connected across the output of the rectifier 314 to filter out high frequency components of the DC voltage. The regulator 318 receives the filtered DC voltage and outputs both a digital supply voltage 330 to operate the hardware logic 324 and an analog supply voltage 332 to operate the electrochemical sensor 320. For example, the analog supply voltage can be a voltage used by the sensor interface 321 to apply a voltage between the sensor electrodes 322, 323 to generate an amperometric current. The digital supply voltage 330 can be a voltage suitable for driving digital logic circuitry, such as approximately 1.2 volts, approximately 3 volts, etc. Reception of the radio frequency radiation 341 from the external reader 340 (or another source, such as ambient radiation, etc.) causes the supply voltages 330, 332 to be supplied to the sensor 320 and hardware logic 324. While powered, the sensor 320 and hardware logic 324 are configured to generate and measure an amperometric current and communicate the results.

The sensor results can be communicated back to the external reader 340 via backscatter radiation 343 from the antenna 312. The hardware logic 324 receives the output current from the electrochemical sensor 320 and modulates (325) the impedance of the antenna 312 in accordance with the amperometric current measured by the sensor 320. The antenna impedance and/or change in antenna impedance is detected by the external reader 340 via the backscatter signal 343. The external reader 340 can include an antenna front end 342 and logic components 344 to decode the information indicated by the backscatter signal 343 and provide digital inputs to a processing system 346. The external reader 340 associates the backscatter signal 343 with the sensor result (e.g., via the processing system 346 according to a pre-programmed relationship associating impedance of the antenna 312 with output from the sensor 320). The processing system 346 can then store the indicated sensor results (e.g., tear film analyte concentration values) in a local memory and/or an external memory (e.g., by communicating with the external memory through a network).

In some embodiments, one or more of the features shown as separate functional blocks can be implemented ("packaged") on a single chip. For example, the eye-mountable device 310 can be implemented with the rectifier 314, energy storage 316, voltage regulator 318, sensor interface 321, and the hardware logic 324 packaged together in a single chip or controller module. Such a controller can have interconnects ("leads") connected to the loop antenna 312 and the sensor electrodes 322, 323. Such a controller operates to harvest energy received at the loop antenna 312, apply a voltage between the electrodes 322, 323 sufficient to develop an amperometric current, measure the amperometric current, and indicate the measured current via the antenna 312 (e.g., through the backscatter radiation 343).

Figure 4A:
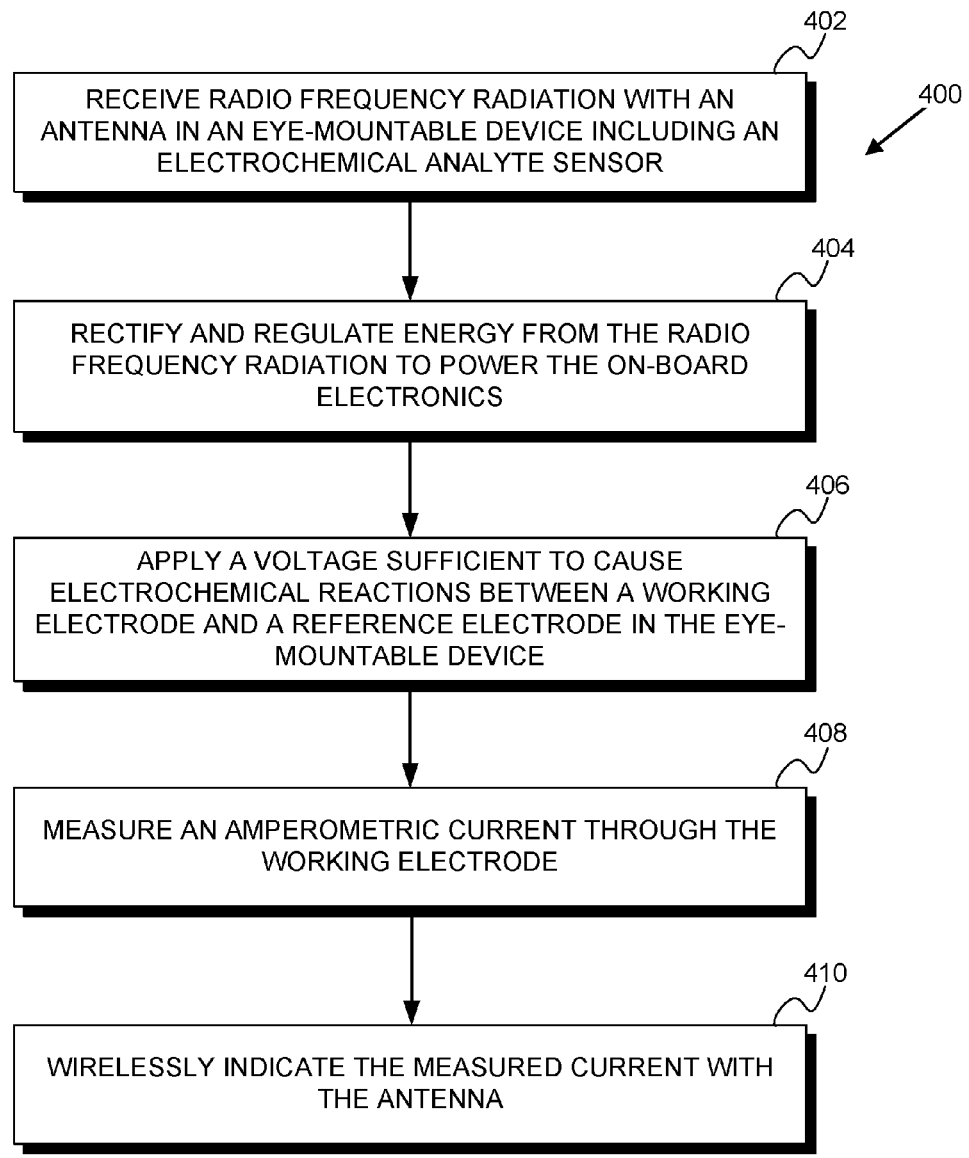
FIG. 4A is a flowchart of an example process for operating an amperometric sensor in an eye-mountable device to measure a tear film analyte concentration.

FIG. 4A is a flowchart of a process 400 for operating an amperometric sensor in an eye-mountable device to measure a tear film analyte concentration. Radio frequency radiation is received at an antenna in an eye-mountable device including an embedded electrochemical sensor (402). Electrical signals due to the received radiation are rectified and regulated to power the electrochemical sensor and associated controller (404). For example, a rectifier and/or regulator can be connected to the antenna leads to output a DC supply voltage for powering the electrochemical sensor and/or controller. A voltage sufficient to cause electrochemical reactions at the working electrode is applied between a working electrode and a reference electrode on the electrochemical sensor (406). An amperometric current is measured through the working electrode (408). For example, a potentiostat can apply a voltage between the working and reference electrodes while measuring the resulting amperometric current through the working electrode. The measured amperometric current is wirelessly indicated with the antenna (410). For example, backscatter radiation can be manipulated to indicate the sensor result by modulating the antenna impedance.

Figure 4B:
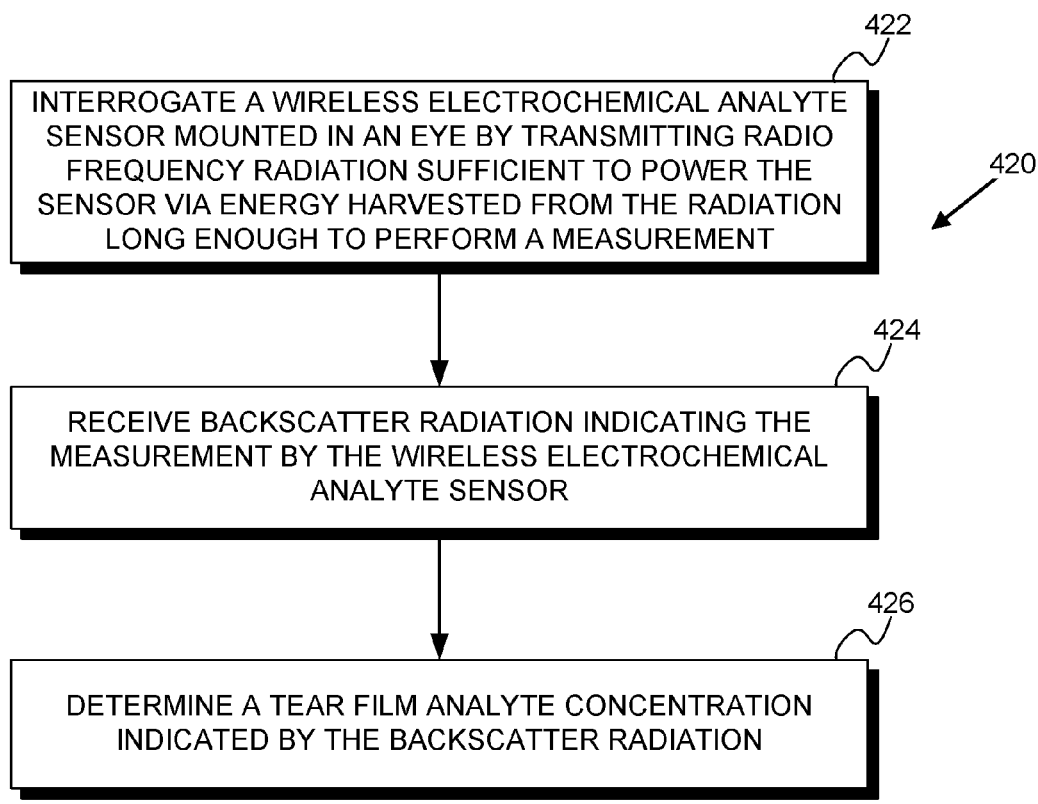
FIG. 4B is a flowchart of an example process for operating an external reader to interrogate an amperometric sensor in an eye-mountable device to measure a tear film analyte concentration.

FIG. 4B is a flowchart of a process 420 for operating an external reader to interrogate an amperometric sensor in an eye-mountable device to measure a tear film analyte concentration. Radio frequency radiation is transmitted to an electrochemical sensor mounted in an eye from the external reader (422). The transmitted radiation is sufficient to power the electrochemical sensor with energy from the radiation for long enough to perform a measurement and communicate the results (422). For example, the radio frequency radiation used to power the electrochemical sensor can be similar to the radiation 341 transmitted from the external reader 340 to the eye-mountable device 310 described in connection with FIG. 3 above. The external reader then receives backscatter radiation indicating the measurement by the electrochemical analyte sensor (424). For example, the backscatter radiation can be similar to the backscatter signals 343 sent from the eye-mountable device 310 to the external reader 340 described in connection with FIG. 3 above. The backscatter radiation received at the external reader is then associated with a tear film analyte concentration (426). In some cases, the analyte concentration values can be stored in the external reader memory (e.g., in the processing system 346) and/or a network-connected data storage.

For example, the sensor result (e.g., the measured amperometric current) can be encoded in the backscatter radiation by modulating the impedance of the backscattering antenna. The external reader can detect the antenna impedance and/or change in antenna impedance based on a frequency, amplitude, and/or phase shift in the backscatter radiation. The sensor result can then be extracted by associating the impedance value with the sensor result by reversing the encoding routine employed within the eye-mountable device. Thus, the reader can map a detected antenna impedance value to an amperometric current value. The amperometric current value is approximately proportionate to the tear film analyte concentration with a sensitivity (e.g., scaling factor) relating the amperometric current and the associated tear film analyte concentration. The sensitivity value can be determined in part according to empirically derived calibration factors, for example.

IV. Assembly of an Example Bio-Compatible Encapsulated Structure

FIGS. 5A-5H illustrate stages in a process to encapsulate electronics in a bio-compatible material. The illustrations shown in FIG. 5A-5H are generally shown in cross-sectional views to illustrate sequentially formed layers developed to create a bio-compatible structure that encapsulates electronics. The layers can be developed by microfabrication and/or manufacturing techniques such as, for example, electroplating, photolithography, deposition, and/or evaporation fabrication processes and the like. The various materials may be formed according to patterns using photoresists and/or masks to pattern materials in particular arrangements, such as to form wires, electrodes, connection pads, etc. Additionally, electroplating techniques may also be employed to coat an arrangement of electrodes with a metallic plating. For example, an arrangement of conductive material formed by a deposition and/or photolithography process can be plated with a metallic material to create a conductive structure with a desired thickness. However, the dimensions, including relative thicknesses, of the various layers illustrated and described in connection with FIGS. 5A-5H to create an encapsulated electronics structure are not illustrated to scale. Instead, the drawings in FIGS. 5A-5H schematically illustrate the ordering of the various layers for purposes of explanation only.

Figure 5A:
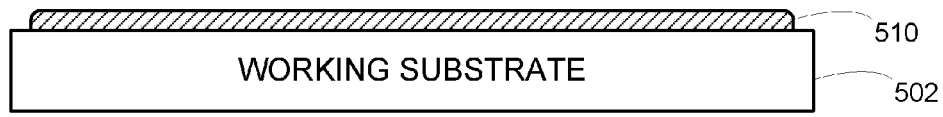
FIGS. 5A-5H show stages of fabricating an example structure in which an electronics module is encapsulated.

FIG. 5A illustrates a working substrate 502 coated with a sacrificial layer 510. The working substrate 502 can be flat surface used to assemble the layers of the encapsulated electronics structure. For example, the working substrate 502 can be a wafer (e.g., a silicon wafer) similar to those used in the fabrication of semiconductor device and/or microelectronics. The working substrate 502 may be a semiconductive material arranged in a crystalline structure (e.g., silicon). The working substrate 502 can generally be a substantially flat material suitable for receiving layers of material by deposition, photolithography, etc. For example, the working substrate 502 may be a silicon wafer with a polished surface. The sacrificial layer 510 can be a material that adheres to the working substrate 502 and provides a surface on which the encapsulated electronics structure can be formed. As discussed further below, during manufacture of the encapsulated electronics structure, the sacrificial layer 510 remains in place until the encapsulated electronics structure is fully formed, and then the sacrificial layer 510 is dissolved and/or rinsed by a rinsing agent to release the encapsulated electronics structure from the working substrate 502. The sacrificial layer 510 thus temporarily attaches the encapsulated electronics structure to the working substrate 502 during assembly, but releases the completed encapsulated electronics structure from the working substrate once assembled.

In some examples, the sacrificial layer 510 can be a positive or negative photoresist or a non-stick coating. The sacrificial layer 510 may include, for example, a silane (e.g., $SiH_4$), a soap, etc. The sacrificial layer 510 can be deposited onto the working substrate with a substantially uniform thickness such that the surface of the sacrificial layer 510 opposite the working substrate 502 forms a flat surface for developing the encapsulated electronics structure.

Figure 5B:
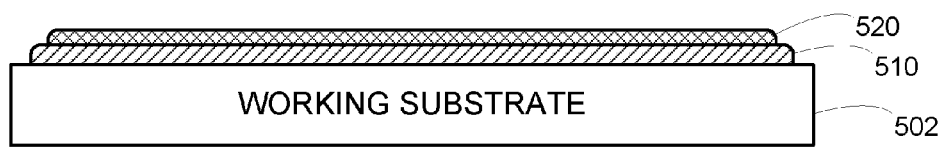

FIG. 5B illustrates a first layer of bio-compatible material 520 formed over the sacrificial layer 510. The first layer of the bio-compatible material 520 can be formed by vapor deposition and can have a thickness of about 1 to about 20 micrometers, for example. The first layer of bio-compatible material 520 forms a first exterior surface of the encapsulated electronics structure, once the structure is fully assembled and released from the working substrate 502.

Biocompatibility refers generally to the ability of a material or device to co-exist with a biological host. In particular, biocompatible materials are generally those that do not bring about a host response (such as an immune response) that result in deleterious effects to either the biological host or the material. Biocompatible materials are therefore used in implantable medical devices and/or surgical instrumentation, because such materials can be situated within the body without causing toxic or injurious effects. Biocompatible materials are also used in objects designed to contact tear film covering the eyes, such as contact lens materials. The bio-compatible material can be a polymeric material including parylene, such as parylene C (e.g., dichlorodi-p-xylylene). Other polymeric materials can also be used, alone or in combination, to form the layer of bio-compatible material 520, such as polyethylene terephthalate (PET), polydimethylsiloxane (PDMS) and other silicone elastomers, etc. By selecting a material that is bio-compatible for the first layer 520, the exterior of the encapsulated electronics structure is able to exist within a biological host. In addition to being bio-compatible, the first layer of bio-compatible material 520 may be an electrically insulating material to isolate the encapsulated electronics from the surrounding environment (e.g., from current-carrying particles and/or fluids).

Furthermore, the electronics to be encapsulated may be assembled directly on the side of the first layer of bio-compatible material 520 opposite the sacrificial layer 510 (i.e., the side of the bio-compatible material that is exposed after forming the first layer of bio-compatible material 520 on the sacrificial layer 510). Thus, the first layer of bio-compatible material 520 can be a substrate for forming electronics. The bio-compatible material can therefore be a material with sufficient structural rigidity to be used as a substrate for assembling electronics by microfabrication processes such as photolithography, etc. However in some embodiments, an additional electronics-assembly substrate can be interposed between the first layer of bio-compatible material 520 and the electronics to be encapsulated. However, the total thickness of the assembled structure can be reduced by using the bio-compatible material itself (e.g., the layer 520) as the electronics assembly surface and thereby avoid inserting an additional layer in the fully assembled structure.

Figure 5C:
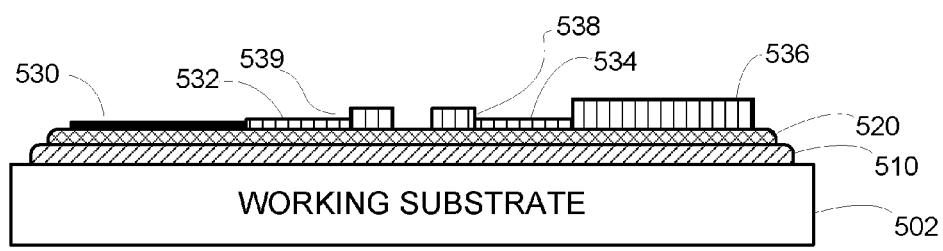

FIG. 5C illustrates an arrangement of conductive material patterned on the first layer of bio-compatible material 520 to form electronics circuitry. The conductive material can be a metal such as platinum, silver, gold, palladium, titanium, copper, chromium, nickel, aluminum, other metals or conductive materials, combinations of these, etc. Some embodiments may employ a substantially transparent conductive material for at least some of the electronics circuitry (e.g., a material such as indium tin oxide). The conductive material is patterned to form wires, electrodes, connection pads, etc., for the circuitry of the embedded electronics created on the layer of bio-compatible material 520. The conductive material can be patterned via photolithography, deposition, and/or electroplating, etc. The pattern can then be electrically connected to additional circuit components, such as chips, to create a bio-interactive electronics module.

For example, metal can be patterned to create components for an electrochemical bio-sensor circuit powered by harvested radio frequency energy, similar to the example electrochemical sensor described above in connection with FIG. 3. In such an example, the metal can be pattered to form sensor electrodes 530, chip-connection pads 538, 539, an antenna 536, and interconnects 532, 534. The sensor electrodes 530 may be electrodes for an electrochemical sensor, for example, similar to the sensor electrodes 322, 323 discussed in connection with FIG. 3 above. The sensor electrodes 530 may include, for example, a reference electrode and a working electrode formed of conductive materials, such as palladium, platinum, titanium, silver, silver-chloride, gold, aluminum, carbon, combinations of these, etc. The sensor electrodes 530 can be arranged in a variety of form factors, such as parallel bars, concentric rings, etc. The working electrode 530 may be a microelectrode, and may have at least one dimension less than 25 micrometers. In one example, the sensor electrodes 530 can be fabricated by patterning a photoresist in a desired arrangement and then evaporating metal to create the sensor electrodes 530 according to the pattern of the photoresist.

The antenna 536 can be a loop antenna suitable for receiving radio frequency radiation harvested to provide a power supply to the electronics. The antenna 536 may be, for example, a loop with a radius of approximately 5 millimeters that is suitable for being arranged around the perimeter of an eye-mountable device, similar to the antenna illustrated and described in connection with FIGS. 2 and 3 above. In some instances, the antenna 536 and/or interconnects 532, 534 can be formed of a metal different from metal used in the sensor electrodes 530 (e.g., the sensor electrodes 530 may be formed of platinum and the antenna 536 may be formed of gold). The sensor electrodes 530, interconnects 532, 534, and the antenna 536 can be formed with a thickness of about 5 micrometers, for example.

The interconnects 532, 534 can be wires formed by photolithography, evaporation, and/or electroplating to connect the sensor electrodes 530 to the chip-connection pad 539. The interconnect 532 provides a low resistance electrical connection between the sensor electrodes 530 and the electrical components within chip 540 (which is shown and described in connection with FIG. 5D). Moreover, while the interconnect 532 is shown schematically as a single wire, multiple interconnects may be used to connect each of a plurality of sensor electrodes to electrical components within chip 540 (e.g., components that function similarly to the sensor interface module 321 illustrated and described in connection with FIG. 3 above). For example, a working electrode and a reference electrode can each be connected, by separate wires, to a potentiostat packaged within chip 540. Similarly, the interconnect 534 provides a low resistance electrical connection between the antenna 536 and the chip-connection pad 538. The interconnect 534 thereby connects the energy harvesting and communication antenna to electrical components within the chip 540 (e.g., components that function similarly to the rectifier module 314 and communication logic 324 illustrated and described in connection with FIG. 3). In some examples, multiple interconnecting wires can connect terminals (e.g., leads) of the antenna 536 to components packaged in the chip 540 (e.g., via respective chip connection pads).

The chip-connection pads 538, 539 can be formed by a process similar to the one described above in connection with the interconnects 532, 534 and the antenna 536. That is, the chip-connection pads 538, 539 can be patterned by a photolithography process and metal can be applied by evaporation and/or electroplating to form the chip-connection pads 538, 539. The chip-connection pads 538, 539 provide a mounting point for the chip 540 to be flip-chip mounted to the pads 538, 539. Accordingly, the chip-connection pads 538, 539 can be patterned to correspond to terminals of the chip 540. Thus, the arrangement of the chip-connection pads may vary depending on the packaging of the chip(s) used in the encapsulated electronics structure.

In some examples, one or more of the metal structures patterned onto the first layer of bio-compatible material 520 can be a multi-layer arrangement that includes a seed layer (or adhesion layer) patterned directly on the bio-compatible material 520. Such a seed layer can be used to adhere to both the bio-compatible material and the bulk of the metal structure that is patterned over the seed layer. For example, such a seed layer may be a material that adheres well to the bio-compatible material, and also serves as a guide to electroplate the remainder of the metal structure.

Figure 5D:
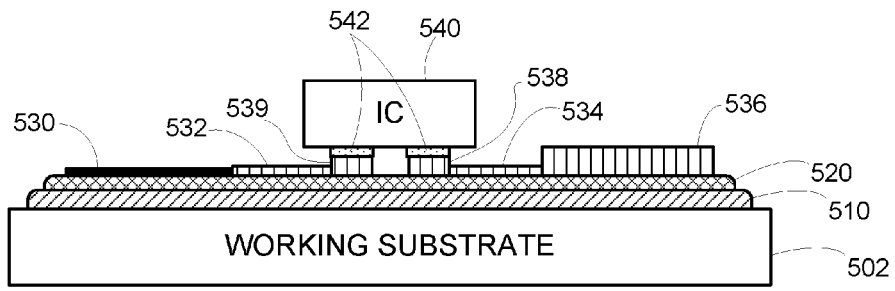

FIG. 5D illustrates a chip 540 mounted to the connection pads 538, 539. Chip 540 could include, for example, one or more integrated circuits (ICs) and/or one or more discrete electronic components. Anisotropic conductive adhesive 542 is applied to the connection pads 538, 539 to facilitate electrical and mechanical connection between the connection pads 538, 539 and corresponding electrodes on the chip 540. The anisotropic conductive adhesive 542 can include an anisotropic conductive film and/or anisotropic conductive paste that is coated on the connection pads 538, 539 by deposition, lithography, etc. The chip 540 can then be flip-chip mounted to the connection pads 538, 539 by positioning the chip 540 with its terminals aligned over the respective connection pads (e.g., the connection pads 538, 539). Once aligned, the chip 540 can be urged toward the connection pads 538, 539 to contact the anisotropic conductive adhesive 542 coating, which adheres to the terminals on the chip 540. The anisotropic conductive adhesive 542 both mechanically adheres the chip 540 to the chip-connection pads 538, 539 and electrically connects the chip 540 to the chip-connection pads 538, 539 (and thus, to the various electrical components connected through the interconnects 532, 534). In some examples, the chip 540 may be mounted to the chip-connection pads 538, 539 using another conductive material such as solder, solder paste, and/or conductive epoxy in addition to, or as an alternative to, the layer of anisotropic conductive adhesive 542.

In some examples, the connection pads 538, 539 may include a solder coating to facilitate electrical and mechanical mounting of the chip 540. For example, while the chip is positioned over the chip-connection pads, the arrangement can be heated to cause the solder to flow and adhere to the terminals of the chip. In some instances, capillary forces of the flowing solder may be used to provide a final fine alignment of the chip 540. Such a solder coating may be used in addition to, or as an alternative to, the anisotropic conductive adhesive 542.

While not specifically shown in FIGS. 5C and 5D, some fabrication processes may include forming a reagent layer over the sensor electrodes 530. The reagent layer may include a substance used to sensitize the sensor electrodes to a particular analyte. For example a layer including glucose oxidase may be applied over the sensor electrodes 530 for detection of glucose.

Figure 5E:
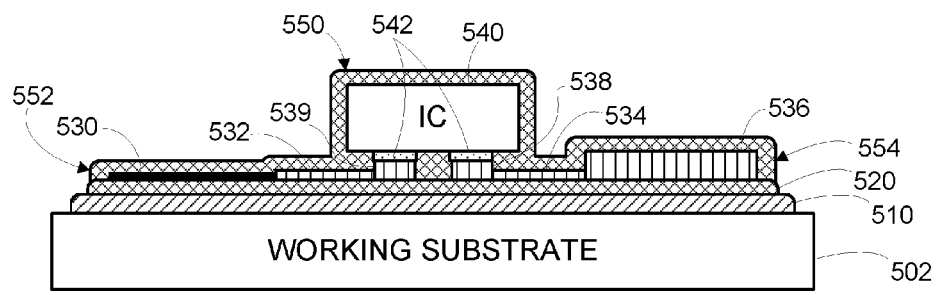

FIG. 5E illustrates a second layer of bio-compatible material 550 formed over the assembled electronics (i.e., the chip 540 and the patterned conductive material forming wires, electrodes, etc.). The second layer of bio-compatible material 550 functions similar to the first layer of bio-compatible material 520 to create a bio-compatible exterior surface and also electrically isolate the electronics from the surrounding environment. In addition, the second layer of bio-compatible material 550 structurally supports the assembled electronics and holds the various components in place. The second layer of bio-compatible material 550 can stabilize the chip 540 by surrounding the chip 540 to fill gaps surrounding the chip 540 (and thereby prevent movement of the chip). In some examples, the deposition of the second layer of bio-compatible material 550 results in a conformal coating over the assembled electronics, as illustrated schematically in FIG. 5E. The second layer of bio-compatible material 550 can have a thickness of about 1 micrometer to about 50 micrometers, for example.

The second layer of bio-compatible material 550 can be formed of the same or substantially similar material to the first layer of bio-compatible material 520 or can optionally be a different polymeric material that is both bio-compatible and electrically insulating.

The second layer of bio-compatible material 550 is preferably deposited to create a continuous layer that spans the entirety of the assembled electronics (i.e., the chip 540 and the patterned conductive material forming wires, electrodes, etc.). The second layer of bio-compatible material 550 can span a region that extends beyond a footprint of the assembled electronics. As a result, the assembled electronics can be surrounded by portions of the second layer of bio-compatible material 550 that rest directly on the first layer of bio-compatible material 520. The schematic illustration in FIG. 5D represents such side edges by the side edge 552 that directly contacts the first layer of bio-compatible material 520 on one side of the sensor electrodes 530 and by the side edge 554 that directly contacts the first layer of bio-compatible material 520 on one side of the antenna 536. The second layer of bio-compatible material 550 can be a substantially continuous, conformal coating over the assembled electronics between the two coatings 552, 554.

Figure 5F:
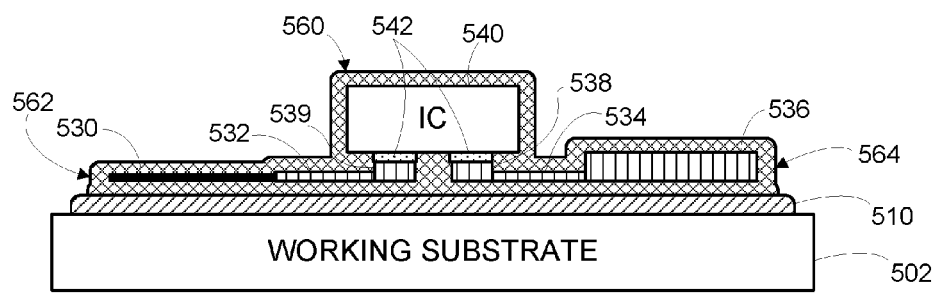

FIG. 5F illustrates the sealed encapsulating layer 560 formed by annealing together the first layer 520 and second layer 550 of the bio-compatible material. The two layers 520, 550 can be annealed together by placing the entire assembled structure, including the working substrate 502, in an oven at a temperature sufficient to anneal the bio-compatible material in the first and second layers 520, 550. For example, parylene C (e.g., dichlorodi-p-xylylene) can be annealed together at a temperature of approximately 150 to 200 degrees Celsius. Other bio-compatible polymeric materials (such as PET, PDMS, etc.) may require higher or lower annealing temperatures.

The annealing process causes regions where the first and second layers are in direct contact, such as at the side edges 552, 554 to flow and seal together. Once cooled, the resulting sealed encapsulating layer 560 is a continuous layer of bio-compatible material that completely encapsulates the assembled electronics within. In particular, following the annealing process, the boundaries between the first and second layers at the side edges 552, 554 are replaced with sealed regions 562, 564 where the former edges are annealed together to completely seal the electronics from the surrounding environment.

During the annealing process, the sacrificial layer 510 separates the bio-compatible material (e.g., the first layer of bio-compatible material 520) from the working substrate 502. Thus, the sacrificial layer 510 can prevent the bio-compatible material from adhering to the working substrate 502 during the annealing process.

Alternatively, the sacrificial layer 510 may be omitted (e.g., where the first layer of bio-compatible material 520 is formed directly on the working substrate 502). Thus, the sealed encapsulating layer 560 may directly contact the working substrate 502. In such an example, the encapsulated electronics structure can be peeled away from the working substrate 502 following the annealing process. The encapsulated electronics structure may also be etched to remove excess bio-compatible material prior to peeling away the structure. For example, bio-compatible material may at least partially wrap around the working substrate 502 either during the deposition process or the annealing process or both. Etching (e.g., with an oxygen plasma) can be used to cut away portions of the bio-compatible material that wrap around the working substrate 502 and also can be used to create a desired shape for the encapsulated electronics structure. In some examples, the encapsulated electronics structure can be peeled away from the working substrate 502 following such an etching process.

Figure 5G:
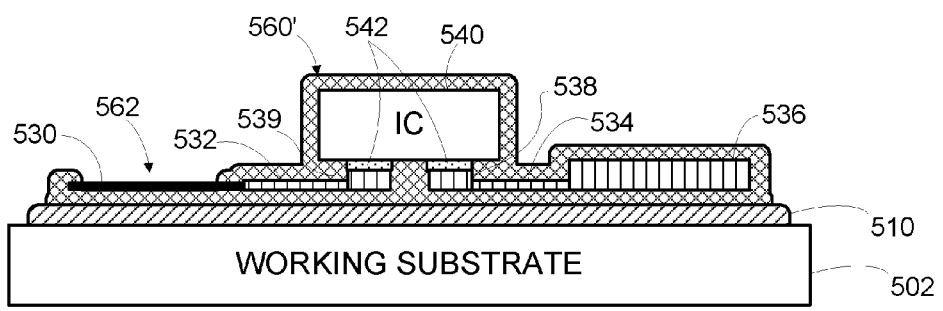

FIG. 5G illustrates an example sensor-revealed encapsulating layer 560'. The sensor-revealed encapsulating layer 560' may be formed by removing a region of the encapsulating bio-compatible material to reveal the sensor electrodes 530. Accordingly, the sensor-revealed encapsulating layer 560' includes an opening 562 in the bio-compatible material on the side opposite the working substrate 502 (e.g., on the side of the encapsulating bio-compatible layer formed by the second layer of bio-compatible material 550). The opening 562 can be formed by removing the region of the bio-compatible material that covers the sensor electrodes 530. The region of bio-compatible material may be removed by treating the region with oxygen plasma, for example.

In some embodiments, the opening 562 that reveals the sensor electrodes 530 is formed by removing material from the side of the bio-compatible material that is used to cover the assembled electronics, and not from the side of the bio-compatible material that is used as a substrate on which to assemble the electronics. In this way, the substrate on which the electronics are assembled (and thus the substrate the electronics are initially mounted to) may be left undisturbed while still allowing the sensor electrodes 530 to be revealed via the opening 562.

In operation, the opening 562 increases the sensitivity of the electrochemical analyte sensor, particularly for analytes that do not readily diffuse through the bio-compatible material. By including the opening 562, analyte concentrations can be measured at the sensor electrodes 530 without diffusing through the bio-compatible material. Thus, when the analyte of interest does not readily diffuse through the layer of bio-compatible material, the opening 562 allows the analyte to reach the sensor electrodes 530 without passing through the encapsulating bio-compatible material.

Figure 5H:
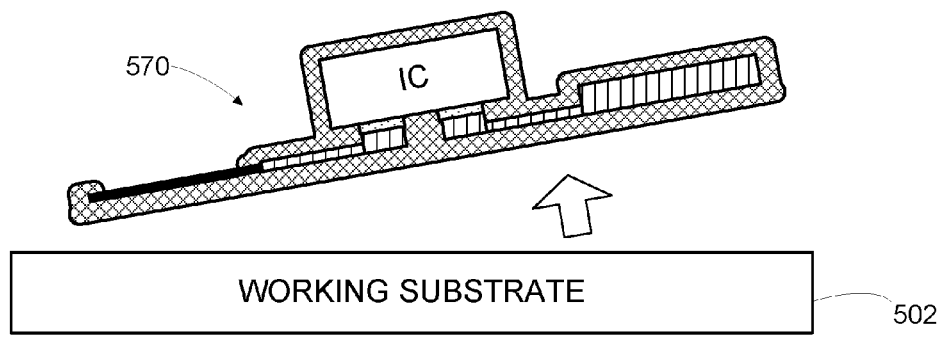

FIG. 5H illustrates an example released encapsulated electronics structure 570. The released encapsulated electronics structure 570 is released from the working substrate 502 by removing the sacrificial layer 510. For example, if the sacrificial layer is a photoresist, the photoresist may be rinsed with a rinsing agent such as acetone, isopropyl alcohol, etc. If the sacrificial layer is a soap film, water may be used to rinse away the soap and release the encapsulated electronics structure 570. Such a rinsing agent may be configured to remove the sacrificial layer 510 without also degrading the bio-compatible material.

The released encapsulated electronics structure 570 is suitable for being incorporated into a biological environment, such as within an eye-mountable device or an implantable medical device, for example. Due to the encapsulating bio-compatible material, the surrounding environment is sealed from the encapsulated electronics. For example, if the structure is implanted in a biological host, or placed in an eye-mountable device to be exposed to tear fluid (e.g., similar to the substrate 230 discussed in connection with FIG. 2 above), the structure is able to be exposed to fluids of the biological host (e.g., tear fluid, blood, etc.), because the entire exterior surface is coated with bio-compatible material that lacks gaps or seams.

In some instances, an additional etching process may be performed prior to releasing the encapsulated electronics structure 570. For example, excess bio-compatible material may be trimmed away from the encapsulated structure by etching the excess material. Additionally or alternatively, the completed encapsulated structure can be separated from neighboring encapsulated structures assembled in parallel on the same working substrate by etching through overlapping regions of annealed bio-compatible material that connect neighboring structures. An oxygen plasma etching process can be used to cut out the encapsulated structure in a desired shape prior to releasing the encapsulated structure. In some examples, the encapsulating bio-compatible material can be etched in the shape of a flattened ring similar to the shape of the substrate 230 illustrated and described in connection with FIG. 2 above, for example.

In some examples, the etching that shapes the encapsulated structure 570 into a ring-shaped structure can also be used to form the opening 562 over the sensor electrodes 530. For example, the bio-compatible material can be a material that is readily removed by oxygen plasma. The oxygen plasma can then be used to form encapsulated structure 570 into a desired shape, such as a ring shape, by directing the oxygen plasma over portions of the bio-compatible material. In contrast, the sensor electrodes 530 can be formed of a material that is not readily etched by the oxygen plasma, so that the sensor electrodes 530 can function as an etch stop. To form the opening 562, the oxygen plasma can remove the bio-compatible material covering the sensor electrodes 530 while leaving the sensor electrodes 530 substantially intact.

Additionally or alternatively, the encapsulated electronics structure 570 may be released from the working substrate 502 by peeling the encapsulated electronics structure 570 away from the working substrate 502. For instance, in an example where the sacrificial layer 510 is omitted, the encapsulated electronics structure 570 may be formed directly on the working substrate 502. The encapsulated electronics structure 570 may be etched to create a ring-shaped structure (or another desired shape for the encapsulated electronics structure) and the encapsulated electronics structure can then be peeled away from the working substrate 502.

The description in FIGS. 5A through 5H describes one example of an assembly process for creating an encapsulated electronics structure suitable for being mounted within an eye-mountable device. For example, the cross-sectional views shown in FIGS. 5A through 5H can be a slice through a flattened ring similar to the flattened-ring-shaped substrate 230 shown and described in connection with FIG. 2 above. In such examples, the encapsulated electronics structure 570 may be mounted within an eye-mountable device, such as within a polymeric material (e.g., a hydrogel material) formed to be contact-mounted to a corneal surface. The electrochemical sensor can then be used to measure the analyte concentration of tear film that absorbs into the polymeric material of the eye-mountable device. However, a similar process can be employed to create bio-compatible encapsulated electronics for other applications. For example, implantable electronic medical devices may be created by assembling electronics on a first layer of a bio-compatible material, a second layer of bio-compatible material can be formed over the electronics, and the two layers can be annealed together to fully encapsulate the electronics within the bio-compatible material. Such an implantable electronic medical device may be formed on a working substrate coated with a sacrificial layer, and may be released from the working substrate by rinsing the sacrificial layer. Such implantable electronic medical devices may include an antenna for communicating information (e.g., sensor results) and/or inductively harvesting energy (e.g., radio frequency radiation). Implantable electronic medical devices may also include electrochemical sensors or they may include other electronic devices.

Some embodiments of the present disclosure relate to an encapsulated electronics structure that includes an electrochemical sensor. For example, a chip connected to sensor electrodes an antenna (e.g., the chip 540 connected to the sensor electrodes 530 and antenna 536) can be configured to apply a voltage across the sensor electrodes, measure an amperometric current through the working electrode, and wirelessly communicate the measured amperometric current with the antenna. In some examples a dedicated module, such as integrated circuit with suitable program logic, interfaces, etc., is packaged in a single chip (e.g., the chip 540), however the functions described above can be carried out by any combination of hardware and/or software implemented modules. Thus, some embodiments of the present disclosure that relate to electrochemical sensors refer to encapsulated electronics that include an antenna and a controller, where the controller is a module configured to carry out one or more of the functions described above.

It is noted, however, that the present disclosure may include electronics modules that are configured to perform functions in addition to, or as alternatives to, those described above. For example, the encapsulated electronics module may include a light sensor, temperature sensor, and/or other sensors useful for detecting diagnostically relevant information in an ophthalmic and/or implantable application. The encapsulated electronics module may, for example, obtain a temperature reading and then communicate the temperature information or use the temperature information to modify a measurement procedure with the electrochemical sensor. Moreover, the encapsulated electronics module can include a combination of capacitors, switches, etc., to regulate voltage levels and/or control connections with other electronics modules. For example, the encapsulated electronics module may include a capacitor for regulating a voltage supply generated by harvesting energy from the antenna, similar to the capacitor 316 described in connection with FIG. 3 above. Thus, some embodiments of the encapsulated electronics module (e.g., the controller and/or antenna) may include a variety of circuit-design and other modifications to achieve functions desired for a particular implementation.

Figure 6A:
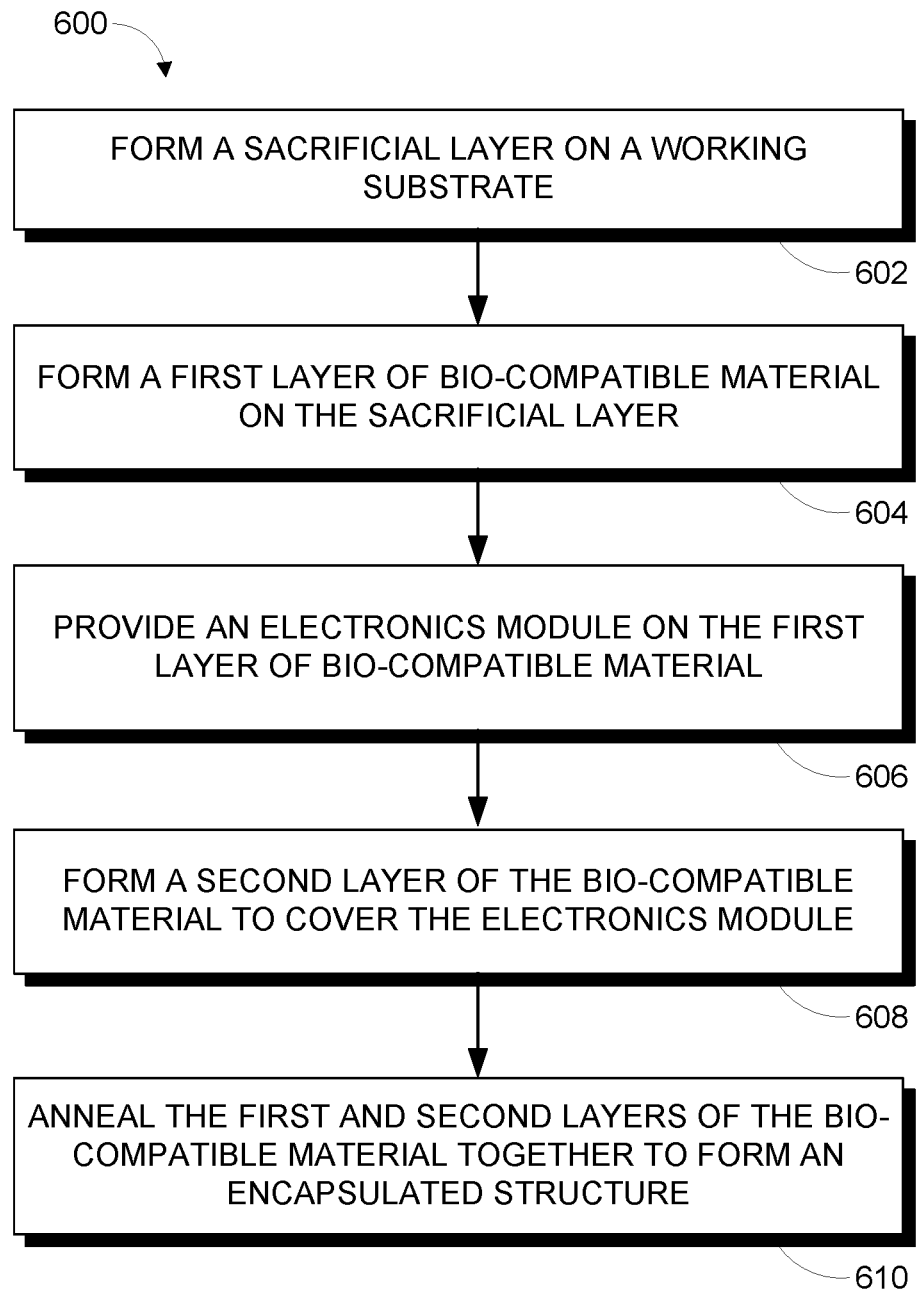
FIG. 6A is a flowchart of an example process for fabricating an encapsulated structure.

FIG. 6A is a flowchart of an example process 600 for producing an encapsulated electronics module. A sacrificial layer is formed on a working substrate (602). The sacrificial layer can be a photoresist, a silane, a non-stick coating, such as a soap film, etc. A first layer of bio-compatible material is formed on the sacrificial layer (604). The first layer of bio-compatible material can include a polymeric material such as parylene C (e.g., dichlorodi-p-xylylene), a polyethylene terephthalate (PET), a polydimethysiloxane (PDMS), other silicone elastomers, and/or another bio-compatible polymeric material. The first layer of bio-compatible material can be formed by a microfabrication process such as deposition, etc. In some examples, the first layer of bio-compatible material is formed with a substantially uniform thickness such that the exposed side of the bio-compatible material (i.e., the side opposite the working substrate) is a substantially flat surface that can be used as a substrate for assembling electronics.

An electronics module is provided on the exposed side of the first layer of bio-compatible material (606). The electronics module can be assembled as described above, for example, in connection with FIGS. 5C and 5D. Thus, the first layer of bio-compatible material can be used as a substrate for assembly of the electronics module thereon. Alternatively, the electronics module could be placed on the first layer of bio-compatible material in a fully or partially assembled form. The electronics module can include patterned metal arranged as wires, electrodes, connection pads, antenna(e), etc. Microfabrication techniques such as photolithography, evaporation, electroplating, etc. can be used to pattern metal in an arrangement suitable for the electronics module. The electronics module can also include one or more integrated circuits, which may be flip chip mounted. In some examples anisotropic conductive adhesive may be used to electrically and mechanically connect terminals of a packaged integrated circuit to corresponding connection pads.

A second layer of bio-compatible material is formed over the assembled electronics module (608). The second layer of bio-compatible material may be a bio-compatible polymeric material that is the same as the first layer of bio-compatible material. The second layer may be formed via a microfabrication technique, such as evaporation, to create a conformal layer over the assembled electronics, and that overlaps the entirety of the assembled electronics such that outer edges of the second layer of bio-compatible material directly contacts the first layer of bio-compatible material. The two layers of bio-compatible material can then be annealed together (610). The annealing process can seal the two layers of bio-compatible material together and thereby encapsulate the assembled electronics within the bio-compatible material.

In some examples, the first layer of bio-compatible material can be formed directly on the working substrate, rather than on the sacrificial layer. For example, a layer of material such as parylene C can be formed directly on a clean silicon wafer. Once a second layer of bio-compatible material is annealed to the first layer so as to encapsulate the electronics module, the encapsulated structure can be peeled away from the working substrate. Thus, the sacrificial layer may be omitted from the assembly process. That is, in some embodiments, the process 600 described in the flowchart of FIG. 6A may omit block 602.

Figure 6B:
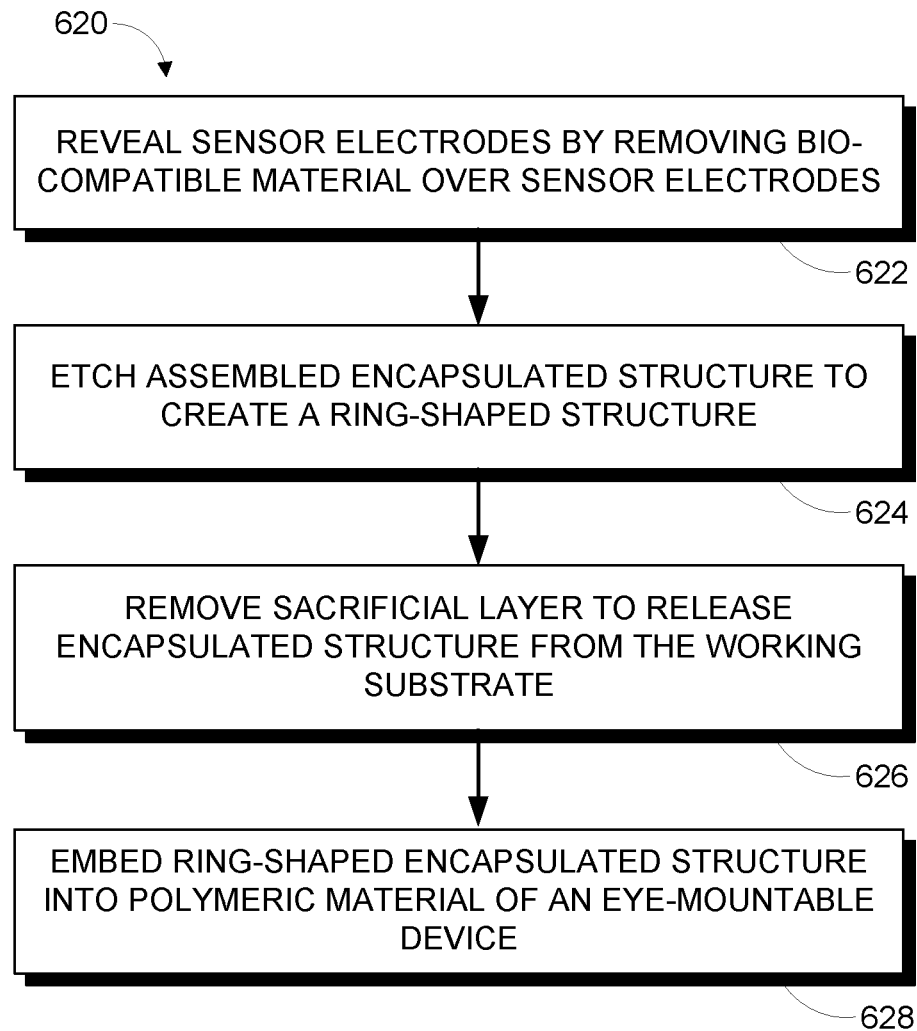
FIG. 6B is a flowchart of an example process for incorporating an encapsulated structure into an eye-mountable device.

FIG. 6B is a flowchart of an example process 620 for incorporating an encapsulated electronics module into an eye-mountable device. The encapsulated electronics module can be etched to remove a region of the bio-compatible material and thereby reveal sensor electrodes (622). Thus, block 622 applies to examples where the encapsulated electronics include an electrochemical sensor with sensor electrodes, and may be omitted if the encapsulated electronics include other bio-interactive electronics. The region can be removed by etching the bio-compatible material with an oxygen plasma, for example. The region of bio-compatible material that is removed may be from the layer of bio-compatible material applied to cover the assembled electronics (e.g., the layer discussed in connection with block 608), rather than the layer applied over the sacrificial layer to create a substrate for assembling the electronics (e.g., the layer discussed in connection with block 604). The electronics modules are initially mounted to the layer of bio-compatible material used as a substrate for assembling the electronics, which is referred to herein for convenience only as the "substrate layer". By leaving the substrate layer of bio-compatible material undisturbed while revealing the sensor electrodes, the initially formed bond between the sensor electrodes and the substrate layer remains intact. Revealing the sensor electrodes without disturbing the initial mounting bonds results in an assembled device that benefits from the structural integrity and resiliency of the initial mounting bonds between the sensor electrodes and the substrate layer of bio-compatible material.

The assembled encapsulated structure can be etched to create a ring-shaped structure (624). For example, the encapsulated structure may be etched to create a flattened-ring-shape similar to the ring-shaped substrate 230 shown and described in connection with FIG. 2 above. The encapsulated structure may also be etched in another shape, such as a rectangle, a circle (e.g., a disc), an oval, etc. to create a generally flat structure in which assembled electronics are encapsulated by sealed bio-compatible material. In some examples, the etching process of block 624 includes cutting through the areas where the two layers of bio-compatible material are annealed together (e.g., as discussed in block 612). Thus, the etching process of block 624 may include cutting through the sealed edges of bio-compatible material that surround the encapsulated electronics. In some examples, the two layers of bio-compatible material (and the working substrate and sacrificial layer) can span a plurality of assembled electronics modules. For example, the working substrate may be divided into a grid, with each unit occupied by an assembled electronics module, and the sacrificial layer and layers of bio-compatible material can be extended across the entire grid in a substantially continuous manner. In such an example, the etching process of block 624 may thus be used to separate the distinct electronics modules from one another by cutting through the annealed bio-compatible material that extends between the separate modules. Following block 624, the resulting encapsulated electronics structure is shaped to be integrated into a biological host environment, such as in an eye-mountable device, an implantable medical device, etc.

The sacrificial layer is removed to release the encapsulated structure from the working substrate (626). The sacrificial layer can be removed by applying a rinsing agent to dissolve the sacrificial layer. For example, acetone or isopropyl alcohol can be applied to dissolve the sacrificial layer and thereby release the encapsulated structure. The rinsing agent is selected to react with the sacrificial layer (e.g., by dissolving), but not react with the bio-compatible material that encapsulates the assembled electronics. In an example with soap film used as the sacrificial layer, water can be used to rinse away the soap film.

The released encapsulated structure can then be embedded into polymeric material of an eye-mountable device (628). Where the encapsulated structure is given a flattened-ring shape (i.e., during the etching processing block 624), the structure can be embedded around the peripheral region of a generally circular polymeric material shaped to be contact-mounted to an eye. Such a polymeric material may have, for example, a concave surface configured to be mounted over a corneal surface of an eye and a convex surface opposite the concave surface configured to be compatible with eyelid motion while mounted to the corneal surface. For example, a hydrogel material (or other polymeric material) can be formed around the encapsulated structure in an injection molding process.

Figure 7:
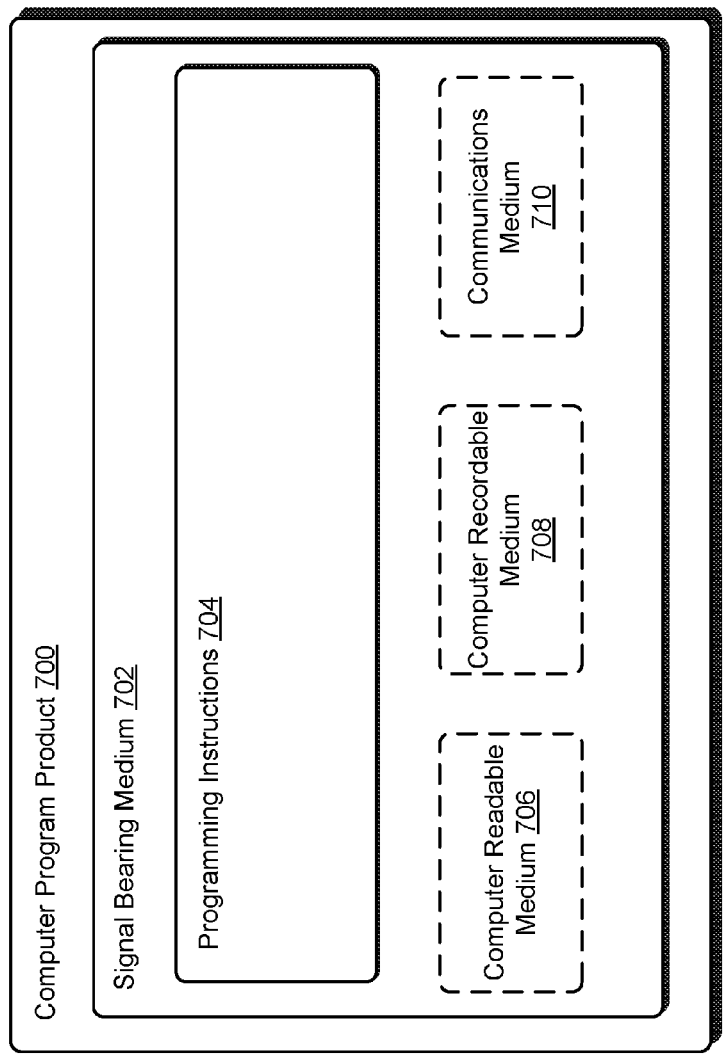
FIG. 7 depicts a computer-readable medium configured according to an example embodiment.

FIG. 7 depicts a computer-readable medium configured according to an example embodiment. In example embodiments, the example system can include one or more processors, one or more forms of memory, one or more input devices/interfaces, one or more output devices/interfaces, and machine-readable instructions that when executed by the one or more processors cause the system to carry out the various functions, tasks, capabilities, etc., described above.

As noted above, in some embodiments, the disclosed techniques can be implemented by computer program instructions encoded on a non-transitory computer-readable storage media in a machine-readable format, or on other non-transitory media or articles of manufacture. FIG. 7 is a schematic illustrating a conceptual partial view of an example computer program product that includes a computer program for executing a computer process on a computing device, arranged according to at least some embodiments presented herein, including the processes shown and described in connection with FIGS. 6A and 6B.

In one embodiment, the example computer program product 700 is provided using a signal bearing medium 702. The signal bearing medium 702 may include one or more programming instructions 704 that, when executed by one or more processors may provide functionality or portions of the functionality described above with respect to FIGS. 1-6. In some examples, the signal bearing medium 702 can include a non-transitory computer-readable medium 706, such as, but not limited to, a hard disk drive, a Compact Disc (CD), a Digital Video Disk (DVD), a digital tape, memory, etc. In some implementations, the signal bearing medium 702 can be a computer recordable medium 708, such as, but not limited to, memory, read/write (R/W) CDs, R/W DVDs, etc. In some implementations, the signal bearing medium 702 can be a communications medium 710, such as, but not limited to, a digital and/or an analog communication medium (e.g., a fiber optic cable, a waveguide, a wired communications link, a wireless communication link, etc.). Thus, for example, the signal bearing medium 702 can be conveyed by a wireless form of the communications medium 710.

The one or more programming instructions 704 can be, for example, computer executable and/or logic implemented instructions. In some examples, a computing device is configured to provide various operations, functions, or actions in response to the programming instructions 704 conveyed to the computing device by one or more of the computer readable medium 706, the computer recordable medium 708, and/or the communications medium 710.

The non-transitory computer readable medium 706 can also be distributed among multiple data storage elements, which could be remotely located from each other. The computing device that executes some or all of the stored instructions can be a microfabrication controller, or another computing platform. Alternatively, the computing device that executes some or all of the stored instructions could be remotely located computer system, such as a server.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. An eye-mountable device, comprising:
   a transparent polymeric material; and
   a substrate at least partially embedded in the transparent polymeric material, wherein the substrate comprises (i) an electrochemical sensor that includes a working electrode and a reference electrode and (ii) an electronics module encapsulated within a bio-compatible material such that tear fluid is isolated from the electronics module by the bio-compatible material, wherein the bio-compatible material includes a first layer and a second layer in which the electronics module is interposed between the first and second layers and portions of the first and second layers are annealed together, wherein the electronics module includes an antenna and a controller electrically connected to the electrochemical sensor and the antenna.

2. The eye-mountable device of claim 1, wherein the controller controls the electrochemical sensor to obtain a sensor measurement related to a concentration of an analyte in tear fluid and uses the antenna to indicate the sensor measurement.

3. The eye-mountable device of claim 1, wherein the working and reference electrodes are disposed on the first layer, and wherein the second layer has an opening over the working and reference electrodes.

4. The eye-mountable device of claim 1, wherein the substrate has a thickness of less than 150 micrometers.

5. The eye-mountable device of claim 1, wherein the substrate is embedded near a periphery of the transparent polymeric material in the eye-mountable device.

6. The eye-mountable device of claim 1, wherein the electronics module includes an energy harvesting system that captures electrical energy from incident radiation to power the electronics module.

7. The eye-mountable device of claim 1, wherein the bio-compatible material includes a dichlorodi-p-xylylene polymer.

8. A method, comprising:
forming a first layer of a bio-compatible material;
providing an electronics module on the first layer of the bio-compatible material;
forming a second layer of the bio-compatible material to cover the electronics module; and
annealing portions of the first and second layers of the bio-compatible material together to form an encapsulated structure; and
etching through the annealed portions of bio-compatible material to form a shaped structure, wherein the shaped structure comprises the electronics module encapsulated in the bio-compatible material.

9. The method of claim 8, further comprising:
forming a sacrificial layer on a working substrate, wherein the first layer of the bio-compatible material is formed on the sacrificial layer; and
removing the sacrificial layer to release the shaped structure from the working substrate.

10. The method of claim 8, wherein the first and second layers of the bio-compatible material and the electronics module have a combined thickness of less than 150 micrometers.

11. The method of claim 8, wherein the first layer of the bio-compatible material, the electronics module, and the second layer of the bio-compatible material are all stacked over a sacrificial layer on a working substrate during the annealing, and wherein the annealing includes baking the working substrate in an oven.

12. The method of claim 8, further comprising:
embedding the shaped structure in a transparent polymeric material to form an eye-mountable device.

13. The method of claim 8, wherein the bio-compatible material includes a dichlorodi-p-xylylene polymer.

14. The method of claim 8, further comprising forming a sacrificial layer on a working substrate, wherein the sacrificial layer separates the bio-compatible material from the working substrate during the annealing.

15. The method of claim 8, further comprising assembling the electronics module, wherein assembling the electronics module comprises:
patterning metal to form connection pads, electrochemical sensor electrodes, an antenna, antenna interconnects between at least one of the connections pads and the antenna, and sensor interconnects between at least one of the connection pads and one or more of the electrochemical sensor electrodes; and
applying a chip to the connection pads.

16. The method of claim 15, wherein the applying the chip to the connection pads includes electrically connecting the chip to the connection pads via an anisotropic conductive adhesive.

17. The method of claim 8, wherein the electronics module includes an energy harvesting system that captures electrical energy from incident radiation to power the electronic components.

18. A device prepared by a process, comprising:
forming a first layer of a bio-compatible material;
providing an electronics module on the first layer of the bio-compatible material;
forming a second layer of the bio-compatible material to cover the electronics module; and
annealing portions of the first and second layers of the bio-compatible material together to form an encapsulated structure; and
etching through the annealed portions to form a shaped structure, wherein the shaped structure comprises the electronics module encapsulated in the bio-compatible material.

19. The device of claim 18, wherein the process further comprises:
forming a sacrificial layer on a working substrate, wherein the first layer of the bio-compatible material is formed on the sacrificial layer; and
removing the sacrificial layer to release the shaped structure from the working substrate.

20. The device of claim 18, wherein the process further comprises:
embedding the shaped structure in a transparent polymeric material.

* * * * *